United States Patent [19]
Green et al.

[11] Patent Number: 5,956,145
[45] Date of Patent: *Sep. 21, 1999

[54] SYSTEM AND METHOD FOR IMPROVING DATA ACQUISITION CAPABILITY IN SPECTROSCOPIC ROTATABLE ELEMENT, ROTATING ELEMENT, MODULATION ELEMENT, AND OTHER ELLIPSOMETER AND POLARIMETER AND THE LIKE SYSTEMS

[75] Inventors: Steven E. Green; Craig M. Herzinger; Blaine D. Johs; John A. Woollam; Stephen P. Ducharme, all of Lincoln, Nebr.

[73] Assignee: J. A. Woollam Co. Inc., Lincoln, Nebr.

[*] Notice: This patent is subject to a terminal disclaimer.

[21] Appl. No.: 09/017,423

[22] Filed: Feb. 2, 1998

Related U.S. Application Data

[63] Continuation-in-part of application No. 08/265,325, Jun. 24, 1994, Pat. No. 5,521,706, application No. 08/515,738, Aug. 16, 1995, abandoned, and application No. 08/422,346, Apr. 14, 1995, Pat. No. 5,757,494, which is a continuation-in-part of application No. 08/327,107, Oct. 21, 1994, Pat. No. 5,582,646, said application No. 08/265,325, is a continuation-in-part of application No. 07/947,430, Sep. 18, 1992, Pat. No. 5,373,359.

[51] Int. Cl.$^6$ .................................................. G01N 21/21
[52] U.S. Cl. ........................................... 356/364; 356/369
[58] Field of Search .................................... 356/364, 365, 356/366, 367, 368, 369; 250/225

[56] References Cited

U.S. PATENT DOCUMENTS

| | | |
|---|---|---|
| 3,594,085 | 7/1971 | Wilmanns . |
| 3,741,661 | 6/1973 | Yamamoto et al. ................... 352/117 |
| 3,880,524 | 4/1975 | Dill et al. ................................ 356/118 |

(List continued on next page.)

OTHER PUBLICATIONS

Ellipsometry & Polarized Light, Azzam & Bashara, North-Holland pp. 152–181 pp. 245–267 pp. 399–416, pp. 370–373, pp. 405–416.

(List continued on next page.)

*Primary Examiner*—Hoa Q. Pham
*Attorney, Agent, or Firm*—James D. Welch

[57] ABSTRACT

Disclosed is a system and method for controlling polarization state determining parameters of a polarized beam of light in an ellipsometer or polarimeter and the like system, (eg. a modulation element ellipsometer system), so that they are in ranges wherein the sensitivity, (of a sample system characterizing PSI and DELTA value monitoring detector used to measure changes in said polarization state resulting from interaction with a "composite sample system," comprised of a sample system per se. and a beam polarization state determining variable retarder, to noise and measurement errors etc. therein), is reduced. The present invention allows determining sample system per se. characterizing PSI and DELTA values, from Composite Sample System characterizing PSI and DELTA values, by compensating for the presence of present invention components, (VR1) and/or VR2), added to an ellipsometer or polarimeter and the like system. The present invention also improves the ability of an ellipsometer or polarimeter and the like system fitted with present invention components (VR1) and/or (VR2) to provide usably accurate and precise sample system characterizing PSI and DELTA determining data values, wherein a sample system per se. investigating polarized beam of light is oriented at other than a Principal or Brewster Angle of Incidence thereto, the use of which Angle of Incidence would otherwise be difficult, if not impossible. Practice of the present invention also allows determination of the "Handedness" of a polarized beam of light, and of sample system Jones or Mueller Matrix component values. As well, the present invention provides means for making system components (VR1) and/or (VR2) added to an ellipsometer or polarimeter and the like system, essentially end user transparent when desired, without removal thereof from said ellipsometer or polarimeter system.

21 Claims, 7 Drawing Sheets

U.S. PATENT DOCUMENTS

| | | | |
|---|---|---|---|
| 4,053,232 | 10/1977 | Dill et al. | 356/118 |
| 4,176,951 | 12/1979 | Robert et al. | 356/33 |
| 4,198,261 | 4/1980 | Busta et al. | 156/626 |
| 4,208,240 | 6/1980 | Latos | 156/627 |
| 4,407,709 | 10/1983 | Enjouji et al. | 204/192 |
| 4,408,889 | 10/1983 | Kleinknecht et al. | 356/355 |
| 4,585,348 | 4/1986 | Chastang et al. | 356/369 |
| 4,758,304 | 7/1988 | McNeil et al. | 156/626 |
| 5,057,781 | 10/1991 | Atkins et al. | 324/635 |
| 5,076,696 | 12/1991 | Cohn et al. | 356/369 |
| 5,091,320 | 2/1992 | Aspnes et al. | 437/8 |
| 5,166,080 | 11/1992 | Schietinger et al. | 437/7 |
| 5,181,080 | 1/1993 | Fanton et al. | 356/381 |
| 5,276,503 | 1/1994 | Hayashi et al. | 356/369 |
| 5,311,285 | 5/1994 | Oshiae et al. | 356/369 |
| 5,313,044 | 5/1994 | Massoud et al. | 219/121 |
| 5,329,357 | 7/1994 | Bernoux et al. | 356/367 |
| 5,335,066 | 8/1994 | Yamada et al. | 356/364 |
| 5,336,385 | 8/1994 | Shimose et al. | 204/298.03 |
| 5,373,359 | 12/1994 | Woollam et al. | 356/328 |
| 5,416,588 | 5/1995 | Ducharme et al. | 356/369 |
| 5,521,706 | 5/1996 | Green et al. | 356/369 |
| 5,582,646 | 12/1996 | Woollam et al. | 118/708 |
| 5,657,126 | 8/1997 | Ducharme et al. | 356/369 |
| 5,757,494 | 5/1998 | Green et al. | 356/369 |

OTHER PUBLICATIONS

Recent Developments in Instrumentation in Ellipsometry Hauge Surface Science, vol. 96, 108, 140 (1980).

Automatic Rotating Element Ellipsome Terr: Calibration, Operation and Real–Time Applications. Rev. Sci. Instrum. 61(8), Aug. 1996.

The Berek Polarization Compensator Model 5540 Users Manual, New Focus Inc Publication.

Optics, Hecht Addison–Wesley Publishing pp. 304–305 pp. 316–323.

Photonics Design & Applications Handbook, $39^{th}$ Ed, 1993 pp. H–412–H–415.

Design and Operation of ETA, an Automated Ellipsometer Hauge & Dill IBM J. of Research and Development vol. 17, No. 6 pp. 471–554 Nov. 1973.

Regression Calibration Method for Rotating Element Ellipsometer, Johns, Thin Solid Films, 234 (1993) pp. 395–398.

Meadowlark Optics Catalog Sheets Liquid Crystal Retarder & pp. 2,3,4,5,8&9.

Optics Guide 5, Meller–Griot Catalog Sheets pp. 14–28–14–34.

Two Channel Polarization Modulation Ellipsometer, Jellison & Modine, Applied Optics, vol. 29, No. 7, Mar. 1990.

Improvements of Phase–Modulated Ellipsometry, Bigan, Rev. Sci. Instrum, 60(1) Jan. 1989.

A Reflectance Anisotropy Spectrometer for Real Time Measurements, Archer et al., Rev. Sci. Instru. 63(11) Nov. 1992.

Errors in Polarization Measurements Due to Static ——Modine et al., Appl. Phys. Comm. 12(1) pp. 121–139, (1993).

Phase–Modulated Ellipsometer Using Fourier Transform ——Canillas et al., Rev. Sci. Instrum., 64(8) Aug. 1993.

SYSTEM AND METHOD FOR IMPROVING DATA ACQUISITION CAPABILITY IN SPECTROSCOPIC ROTATABLE ELEMENT, ROTATING ELEMENT, MODULATION ELEMENT, AND OTHER ELLIPSOMETER AND POLARIMETER AND THE LIKE SYSTEMS

The present Application is a CIP of patent application Ser. No. 8/265,325 filed Jun. 24, 1994 which was a CIP of application Ser. No. 07/947,430, filed Sep. 18, 1992 (now U.S. Pat. No. 5,373,359); and of patent application Ser. No. 08/515,738 filed Aug. 16, 1995 (abandoned); and of patent application Ser. No. 08,/422,346 filed Apr. 14, 1995, (now U.S. Pat. No. 5,757,494), which is a CIP of patent application Ser. No. 08/327,107 filed Oct. 21, 1994, (now U.S. Pat. No. 5,582,646), which later Application discloses the use of other than a "Principal" or "Brewster" angle in data acquisition.

TECHNICAL FIELD

The present invention relates systems and methods for improving the data acquisition capability of ellipsometer or polarimeter and the like systems. The present invention is a system and method for controlling the polarization state of a beam of polarized light in, for instance, a spectroscopic ellipsometer, to place measured ellipsometric ratio of orthogonal, (exemplified as "P" and "S" hereinafter), components, and retardation phase angle between said orthogonal components, into ranges in which said spectroscopic ellipsometer is capable of providing usably accurate and precise Sample System characterizing PSI and DELTA determining data, resulting from reduced PSI and DELTA determining procedure sensitivity to noise and measurement errors etc. therein. Stated otherwise, the present invention is a system and method of simulating, in combination with a Sample System per se., a "Composite Sample System", which Composite Sample System presents with characterizing PSI and DELTA values which are in ranges in which, for instance, a spectroscopic ellipsometer system is able to provide usably accurate and precise determining data therefore. The present invention provides that in use, the effects of said present invention system can be compensated for, (eg. subtracted out or otherwise), to provide Sample System per se. characterizing PSI and DELTA values. With only user adjustment present invention system elements, as opposed to replacement thereof, the present invention allows investigation of Sample System per se. characterizing PSI and DELTA values in ranges thereof otherwise difficult, if not impossible to investigate; allows usably accurate and precise acquisition of Sample System characterizing PSI and DELTA value determining data in appropriate ranges, over a relatively large range of wavelengths; allows usably accurate and precise data in appropriate ranges to be acquired when a Sample System investigating polarized beam of light is oriented at other than a Principal or Brewster angle of incidence to a Sample System; allows determination of the "Handedness" of a Sample System; and provides means for determining Jones or Mueller Matrix components of a Sample System. The present invention also provides means for conveniently making present invention system components added to conventional ellipsometer or polarimeter and the like systems essentially end user transparent when desired, without the requirement of inconvenient removal thereof from said conventional ellipsometer or polarimeter and the like systems.

BACKGROUND

While the present invention can be applied to, for instance, any Ellipsometer or Polarimeter and the like System, Spectroscopic Ellipsometers (SE's) will be utilized as a primary, and very relevant, example herein.

Spectroscopic ellipsometer (SE) systems for use in the investigation and characterization of physical and optical properties of Sample Systems over a large range of wavelengths, are well known. Briefly, such (SE) systems operate by monitoring changes effected in the polarization state of a beam of light when said beam of light is caused to interact with a sample system (SS).

Spectroscopic ellipsometer (SE) systems typically comprise a Polarization State Generator, and a Polarization State Detector. In use, the polarization State Generator causes a beam of light in an intended state of polarization to be incident upon a Sample System (SS) at a set Angle of Incidence (AOI), and the Polarization State Detector monitors a reflected and/or transmitted beam of light which emerges from said Sample System (SS) and at least partially determines the polarization state thereof. (Note that a completely defined "Polarization State" of a polarized Light Beam requires designation of intensity ratio and retardation phase angle between quadrature components thereof, as well as an absolute reference intensity, and the "Handedness", (direction of rotation), thereof. Typical Rotating Element Ellipsometers (REE's) determine only a partial polarization state consisting of an intensity ratio and phase angle.)

Continuing, Spectroscopic Ellipsometer (SE) systems fall into general categories such as:

a. Rotatable Element Nulling Ellipsometers (RENE);
b. Rotatable Element Automated Nulling Ellipsometers (REANE));
c. Phase Modulation Ellipsometers (PME);
d. Rotating Analyzer Ellipsometers (RAE);
e. Rotating Polarizer Ellipsometers (RPE);
f. Rotating Compensator Ellipsometers (RCE);
g. Rotating Polarizer and Analyzer Ellipsometers (RPAE);
h. Rotating Polarizer and Analyzer, Fixed Compensator Ellipsometers (RPAFCE);
i. Rotating Analyzer and Compensator, Fixed Polarizer Ellipsometers (RACFPE);
j. Rotating Polarizer and Compensator, Fixed Analyzer Ellipsometers (RPCFAE);
k. Rotating Analyzer, Fixed Polarizer and Compensator Ellipsometers (RAFPCE);
l. Rotating Polarizer, Fixed Analyzer and Compensator Ellipsometers (RPFACE);
m. Rotating Compensator, Fixed Analyzer and Polarizer Ellipsometers (RCFAPE);
n. Rotating Analyzer and Compensator, Fixed and Polarizer (RACFPE).

(Note that similar definitive descriptions also apply to Polarimeter and the life Systems).

The above, non-exhaustive, catagorization is based upon what system components are present and how said system components are used. It is noted that a review Article by Collins, Rev. Sci. Instrum. 61 (8), August 1990 provides a discussion of various ellipsometer configurations.

Generally, all Ellipsometer Systems include elements comprising:

a. a source of a beam of light;
b. a means for imposing an intended state of polarization thereto;
c. a detector system for use in developing a signal from said beam of light after it interacts with said Sample System, which signal contains information that allows determination of optical and physical properties of said Sample System, and d. a means for analyzing said developed signal after it interacts with a Sample System.

While the present invention is applicable to essentially all types of Ellipsometer or Polarimeter and the like systems which contain Rotatable, Rotating, and/or Modulation elements, the present Disclosure will use, as a non-limiting example, a J.A. Woollam Co. Inc. Variable Angle Spectroscopic Ellipsometer (VASE—Registered Trademark), (RAE) system. It is emphasized, however, that the general principals involved in the present invention are generally applicable to any Ellipsometer or Polarimeter and the like system which contains rotatable, rotating and/or modulation elements, examples of which were listed infra.

In more detail then, a Spectroscopic Rotating Analyzer Ellipsometer (RAE) system comprises 1. A Polarization State Generator (PSG) System, comprising:

a. a source of a beam of light, the wavelength of which beam of light can be determined by a user;

b. a Polarizer (P) for use in setting a polarization state in said beam of light provided by said source of a beam of light.

2. A Polarization State Detector (PSD) System, comprising:

a. a Rotating Analyzer (RA), for use in processing said polarized beam of light after it interacts with a Sample System (SS), that a linearly polarized beam of light of varying intensity is produced; and b. a Detector System (DET) for use in developing a signal from said beam of light after it emerges from said Rotating Analyzer (RA), which signal contains information which allows determination of the optical and physical properties of said Sample System.

A typical procedure utilizing a conventional (RAE) system to determine the optical and/or physical properties of a Sample System (SS) involves the steps of:

a. providing a beam of light of an intended wavelength from said source of a beam of light;

b. orienting said beam of light so that it approaches a present Sample System (SS), optical and/or physical properties of which are to be determined, at an Angle Of Incidence (AOI) near the "Principal" or "Brewster" angle for said Sample System (SS);

c. setting the Polarizer (P) to a known fixed position, so that its Azimuth is oriented so as to impose a desired state of polarization upon said beam of light;

d. causing said beam of light, after interaction with said Sample System (SS) to pass through said Rotating Analyzer (RA) and emerge therefrom as a modulated, typically varying intensity with time, beam of light; and e. causing said typically time varying intensity beam of light to enter a Detector System (DET), which Detector System (DET) produces a signal, the analysis of which allows determination of the optical and/or physical properties of the Sample System (SS).

While not a focus of the present invention, previous work by the J.A. Woollam Co. Inc. has determined that it is preferable to apply a non-linearly, (eg. elliptically and preferably essentially circularly polarized), beam of light to a Detector Element (DE). This is because typical Detector Elements demonstrate undesirable Polarization Dependent Sensitivity characteristics. That is, typical Detector Elements respond differently to equal intensity polarized light beam in states of polarization, (eg. the elliptical or linear orientation of a beam), and thereby introduce Detector Element caused errors to resulting determined values which do not represent optical and/or physical Sample System properties per se. Said Detector Element operational inconsistency is, however, in typical Detector Elements, minimized when an essentially circularly polarized or even a non-polarized beam of light is applied thereto, rather than linearly polarized beam of light, such as that which emerges from a Rotating Analyzer (RA). It is noted that linearly polarized light is converted to elliptically polarized light by passage through a Birefringent Retarder which serves to adjust the phase angle between well known "P" and "S" components in a polarized beam of light. (Note, "P" refers to that component of a polarized beam of light in a plane containing the normal to a Sample System and the incident and reflected or transmitted beams, while "S" refers to that component perpendicular thereto, and parallel to the surface of said sample system. Also, it is noted that past a Rotating Analyzer (RA), the relevance of "P" and "S" components is generally lost and it in typical practice Light Beam components are then defined by a coordinate system imposed with respect to a Detector Element rather than a Sample System).

Continuing, it is to be understood that the Rotating Analyzer Ellipsometer example (RAE) system described above, typically is best applied when a beam of polarized light is oriented so that it impinges upon a Sample System (SS) at the "Principal" or "Brewster" Angle Of Incidence (AOI), (note that the terms "Principal" and "Brewster" are used interchangably in this Disclosure), where the measured ellipsometer ellipsometric BETA parameter is essentially zero (0.0) and Sample System characterizing DELTA values are ideally near ninety (90) degrees. (Note that Principal and Brewster Angles refer to a condition whereat DELTA becomes ninety (90) degrees and note that BETA, and ALPHA, are Sample System characterizing values from which PSI and DELTA can be determined by direct application of a transfer function, or by indirect mathematical regression applied to a multiplicity of measured ALPHA-BETA pairs). If the (AOI) is set away from the Brewster Angle, (which for semiconductors is approximately seventy-five (75) degrees), the quality, (eg. usable accuracy and precision), of data obtainable from a (RAE) as indicated infra is degraded. The requirement for operation at the Brewster Angle thus sets a serious limitation on the utilizations of (RAE's). Prior work by the J.A. Woollam Co. Inc. has determined that data obtained from a (RAE) in which the (AOI) is set in excess of the Brewster Angle, can, in some circumstances be of a sufficient quality to allow use in measuring Sample System PSI and DELTA values. Such is the topic in Copending patent application Ser. No. 08/327,107 from which this Application is a CIP. However, the further away an (AOI) is from the Brewster Angle, the more difficult it is to obtain usably precise and accurate data, and any data acquired has associated therwith a greater uncertainty as regards its accuracy, (ie. confidence the data is accurate is lower, and associated possible error greater). It should also be appreciated that the Brewster Angle depends on wavelength such that the ideal Angle Of Incidence (AOI) for one wavelength is not necessarily ideal at another. As a result, when a relatively large range of polarized light beam wavelengths is utilized it is typically necessary to adjust the Angle Of Incidence (AOI) to maintain a Brewster Angle over said relatively large range. It would be very convenient if this (AOI) did not have to be so adjusted as utilized polarized light beam wavelengths are changed. (Note it is to be understood that operation of an Ellipsometer System set to effect a Brewster Angle (AOI) between a polarized Beam of Light and a specific Sample System effects a DELTA of ninety (90) degrees and accompanying circular polarization in the reflected polarized Beam of Light. This is always optimum in that data obtained is accurate to within tighter limits than is possible if data is obtained with other than said polarized Light Beam-Sample System associated Brewster Angle. The present invention does not modify that basic relationship. What the present invention does do, however, is enable better Sample System PSI and DELTA data to be obtained using other than a Brewster Angle, because PSI and DELTA transfer function, (ie. a function which provides PSI and/or DELTA given ALPHA and/or BETA), sensitivity to noise and measurement errors in ALPHA and/or BETA is reduced by setting ALPHA and/or BETA values in ranges where said transfer function is less sensitive to said noise and measurement errors in ALPHA and/or BETA.)

It would be also be of benefit if any (AOI) could be utilized in an Ellipsometer System without unnecessarily limiting the Spectroscopic capability thereof. For instance, the J.A. Woollam VASE (RAE) system operates over a range of at least one-hundred-ninety (190) to seventeen-hundred (1700) nanometers, but because of physical constraints imposed by real-time-in-situ Sample System Processing Systems to which the (VASE)™ is applied, it is not always convenient, or even physically possible, to set an appropriate Brewster (AOI) for a particular polarized light beam wavelength within said range. Restriction on possible (AOI's) then enter undesirable restrictions as to what polarized light beam wavelengths can be utilized and still allow the obtaining of data of a usable accuracy and precision to allow accurate determination of Sample System characterizing PSI and DELTA values therefrom. Again, it would be of benefit if any (AOI) could be used with essentially any polarized light beam wavelength without decreasing the capability to acquire sufficiently usably accurate and precise Sample System PSI and DELTA determining data.

As well, it is noted that typical Ellipsometers, such a described infra, are incapable of determining components of, for instance, a Jones or Mueller Matrix for a Sample System. (Ellipsometry, Polarimetry, Jones and Mueller Matricies, as well as Stokes Vectors and aspects of polarized light and utilization thereof etc., are described in references such as the text titled "ELLIPSOMETRY AND POLARIZED LIGHT", by Azzam and Bashara, North-Holland, 1977, which reference is incorporated by reference into this Disclosure). To obtain up to fifteen (15) of sixteen (16) Mueller Matrix elements, (with the sixteenth being a absolute reference value to which the other fifteen (15) are referenced in a ratio relationship), it is required that one or more Retarders be placed between the Polarizer (P) and Rotating Analyzer (RA) in Rotating Analyzer Ellipsometer (RAE) system, for instance. However, said Retarder(s) have effects on the polarization state of a polarized beam of light, which effect is not always desired. (It is noted that similar use of Retarders is applicable in any type Ellipsometer system). In known Ellipsometer Systems with such Retarder (s) present, undesired effects of said presence, including introduction of artifacts, can not be conveniently minimized. In particular, said Retarders introduce changes in the polarized beam polarization state, which changes are dependent upon wavelength, which dependence limits useful spectroscopic range. In known Ellipsometer Systems said Retarder (s) must be removed therefrom if the effects thereof are to be avoided. The ability to conveniently make one or more Retarders within an Ellipsometer System, end user "Transparent", over a large range of polarized light beam wavelengths, without removal thereof, would alone provide utility in the form of user convenience. That is, no known Ellipsometer System provides such Retarders in a manner such that they can conveniently be made to be essentially end-user "Transparent" by simple user adjustment, as opposed to removal thereof from said Ellipsometer System, over a large range of wavelengths and polarized beam of light (AOI's), emphasis added.

In addition, it is noted that it is difficult to determine the "Handedness", (eg. direction of rotation), of the polarization of a polarized beam of light used in a typical (REE). It would be of benefit to be able to conveniently identify "Handedness" as a natural consequence of the presence of present invention enabling additional components.

Continuing, it is known in the practice of ellipsometry, to adjust the Azimuth Angle (POL) of a Polarizer (P) in a (RAE), (or the Analyzer in an (RPE)), system for instance, to adjust the value of a measured ellipsometric ALPHA to be within a range in which the sensitivity of a PSI Transfer function, (which is known to be a function of said ellipsometric ALPHA), to noise and errors in measurement etc. in measured ellipsometric ALPHA are made essentially negligible. (Note, ALPHA relates to a Magnitude ratio of polarized light beam Quardrature Components in (REE's)). It has not however, to the Inventor's knowledge, been possible to perform a related procedure to adjust ellipsometric BETA to optimum values over a relatively large spectral range of wavelengths, (eg. one-hundred-ninety (190) to seventeen-hundred (1700) nanometers or greater), without introducing unwanted, difficult to compensate artifacts onto a polarized beam of light, without the inconvenient necessity to change elements in said (REE). (Note, BETA relates to a retardation phase angle present between polarized light beam quadrature components in (REE's)).

For instance, using an (RAE) as an example, it would be of great utility were it possible to adjust the measured value if ellipsometric BETA to be within a range in which the sensitivity of a DELTA determining transfer function, (which is known to be a function of ellipsometric ALPHA and ellipsometric BETA), to noise and measurement errors etc. in measured ellipsometric ALPHA and ellipsometric BETA, is made essentially negligible. It would be especially convenient if such could be achieved by placing Varaible Retarder(s) between a Polarizer (P) and an Analyzer (A) in a (REE), such as required to allow obtaining Jones or Mueller Matrix components, which Retarder(s) would allow setting a measured ellipsometric BETA value within a range in which DELTA Transfer function sensitivity to noise and errors in measurement etc. of ellipsometric BETA are made essentially negligible, emphasis added. (It is noted that where ellipsometric ALPHA and ellipsometric BETA are each near zero (0.0) the modulation amplitude of detected intensity in an (REE) system is minimal).

In view of the above, it can be concluded that a system and method of its use which would allow usably accurate and precise data to be achieved from an Ellipsometer or Polarimeter and the like System of any type over a large, continuously variable range of wavelengths and/or (AOI's); and which would allow setting a Polarization State in a Polarized Light Beam, (or alternatively stated, simulating a "Composite Sample System" which presents with a PSI and DELTA in ranges in which they can be accurately measured), such that measured Amplitude Ratio and retardation Phase Angle between Polarized Light Beam Quadrature Components are set in ranges wherein the sensitivity of PSI and DELTA transfer function to noise and measurement errors etc. in, for instance, measured ALPHA and BETA values, are made essentially negligible, would be of great utility. It would be of further utility if said system and method of its use could, as a natural consequence of the presence and utilization thereof respectively, be adapted to allow determination of Jones or Mueller Matrix components. It would also be of utility if an Ellipsometer or Polarimeter and the like system, adapted with present invention system could, by simple user adjustment, be oriented so that added elements were made essentially end user transparent, thereby allowing use of an adapted Ellipsometer or Polarimeter and the like System in an essentially unadapted mode, without requiring that any elements be removed therefrom. It is emphasized that it would especially be of utility if said adapted Ellipsometer or Polarimeter and the like System could be conveniently utilized over a relatively large range of wavelengths without the necessity of System Component replacement.

A Search for relevant Patents which describe systems and/or methods which might be capable of providing the identified utility produced very little. In view of the fact that the present invention system, as is described supra in this Disclosure, in the Disclosure and Detailed description Sections, comprises Variable Retarder(s) (VR's) placed between a Polarizer and Analyzer in a Spectroscopic Rotating Element Ellipsometer, which Variable Retarders (VR's) are effective over relatively large spectral and Angle of Incidence ranges, the Search was focused upon systems which might be interpreted to provide said elements at said locations, or the equivalent effects thereof. Identified Patents are U.S. Pat. No. 3,741,661 to Yamamoto et al.; U.S. Pat. No. 4,176,951 to Robert et al.; U.S. Pat. No. 5,181,080 to Fanton et al.; U.S. Pat. No. 5,311,285 to Oshige; U.S. Pat. No. 5,335,066 to Yamada et al. Also U.S. Pat. No. 4,053,232 to Dill et al; and U.S. Pat. No. 5,329,357 to Bernoux et al. were identified. None of said Patents are considered to be particularly relevant. Patents which describe ellipsometers to which the present invention can be applied are, for instance, U.S. Pat. No. 5,373,359 to Woollam et al., and U.S. Pat. No. 5,416,588 to Ducharme et al., which Patents apply to Rotating Analyzer and Modulator Ellipsometers respectively, were also identified. Another identified Patent, to Dill et al., U.S. Pat. No. 3,880,524, describes the use of a quarter-waveplate Compensator between a Polarizer and a Rotating Analyzer in a Rotating Analyzer Ellipsometer (RAE), such that the state of pollarization of a reflected beam of light from a Sample System can be varied arbitrarily by merely adjusting the angular position (azimuths) of the Polarizer and said quarter-waveplate Compensator. Said quarter-waveplate compensator an be placed ahead or after a Sample System. The system described in Dill et al. provides a means for adjusting both ellipsometric ALPHA and ellipsometric BETA in a polarized beam of light, which polarized beam is "monochromatic". No teachings as how to conveniently make said system applicable over a relatively large spectroscopic range of wavelengths, however, is present. It is emphasized that the Dill et al. 524 Patent is to a monochromatic system, with no convenient provision for expanding to a relatively large spectral range without system element replacement, (that is, a different quarter-wave-plate would be required at each wavelength utilized, and a user would have to disassemble the Dill et al. ellipsometer system and replace such each time a different wavelength was used). The above referenced book by Azzam and Bashara briefly mentions the use of a Variable Retarder, (Babinet-Soleil type), to control relative retardation of Quadrature Components in a polarized Light Beam in Nulling Ellipsometers, but discourages such use because of associated poor resolution capability, (see page 166, footnote 9). Additionally, no teachings were found as how to make added system elements essentially end-user "transparent" at a desired wavelength, cover a large range of wavelengths, without removal thereof from said Ellipsometer System. This is a very important point. Also disclosed is an Article by Johs, titled "Regression Calibration Method For Rotating Element Ellipsometers, Thin Solid Films, 234 (1993). This article describes a regressions approach to calibration of rotating element ellipsometers, and is relevant to the present invention, as the present invention, in part, utilizes a mathematical regression procedure to indirect evaluation of PSI and DELTA Sample System Charaterizing parameters, and is incorporated herein by reference. Another article, which is also incorporated herein by reference, titled "Data Analysis for Spectroscopic Ellipsometry ", by Jellison Jr., Thin Solid Films, 234, ( 1933) p. 416–422, is identifed as it describes a method of determining the accuracy with which certain data points, (for instance, ALPHA or BETA values), can be measured, which information allows adding a weighting factor to a curve fitting regression procedure as applied to a multiplicity of said data, which weighting factor serves to emphasise the effect of more accurate and precise data.

While prior art describes the use of Variable Retarders in Ellipsometer or Polarimeter and the like Systems, none known to, the Inventors describes the application of relatively low Polarization State Artifact introducing Variable Retarder(s) to allow user adjustment of the Polarization State of an investigatory polarized beam of light in an Ellipsometer or Polarimeter and the like System, such that a "Composite Sample System" comprised of a seriesed combination of said relatively low Artifact introducing Variable Retarder and a Sample System per se. can be investigated over a full range of Sample System characterizing PSI and DELTA values, (including Sample Systems with PSI and DELTA values in ranges wherein said Ellipsometer or Polarimeter and the like System normally has difficulty in making measurements, (eg. DELTA's near zero (0.0) and one-hundred-eighty (180) degrees in Rotating Analyzer, Rotating Polarizer and Modulation Ellipsometers). In addition, no prior art obviates the capability of relatively low Polarization State Artifact introducing Variable Retardre(s) to enable Ellipsometer or Polarimeter and the like Systems to be operated over a large range if polarized light beam wavelengths, (eg. one-hundred-ninety (190) to seventeen-hundred (1700) nanometers), with only user adjustment of Variable Retarder(s) being required, rather than replacement thereof, nor does any prior art obviate the capability of low Polarization Variable Artifact introducing Variable Retarder (s) to enable Ellipsometer or Polarimeter and the like Systems to provide usably accurate and precise data when polarized light beams therein are oriented at other than a Principal or Brewster angle with respect thereto.

There is then demonstrated a need for a convenient to use system and method for improving data acquisition capability of spectroscopic ellipsometer and polarimeter and the like systems.

The present invention meets the identified need.

DISCLOSURE OF THE INVENTION

Stated most generally, the present invention system and method of use allows controlling the polarization state of a polarized beam of light in, for instance, a Spectroscopic Ellipsometer System or Polarimeter and the like System, utilized to determine Sample System characterizing PSI and DELTA values, so that associated Polarization State Detector sensitivity to noise and measurement errors is decreased.

More specifically, the present invention is a system and method of use thereof, which allows conveniently obtaining usably accurate and precise Sample System characterizing PSI and DELTA determining data from, for instance, Ellipsometer or Polarimeter and the like Systems, over a relatively large range of wavelengths, and/or in which polarized light beams therein are not necessarily oriented at, or even near, the optimum Principal or Brewster Angle with respect to a Sample System (SS).

To accomplish the stated results the present invention allows controlling not only the range of measured ellipsometric relative magnitude ratio of orthogonal, (hereinafter identified as "P" and "S" in a non-limiting aide to discussion), components of a polarized beam if light during use, but also, simultaneously, the range of the phase angle, (eg. relative retardation), therebetween. (Note that the "P" component refers to that component which is in the plane containing the normal to a Sample System surface and the incident and reflected or transmitted beam(s) of light, and the "S" component is perpendicular thereto and parallel to the surface of a Sample System). For example, where Rotating Analyzer or Rotating Polarizer Ellipsometers are involved, the present invention is a system and method of use which allows a user to set not only measured ellipsometric ALPHA, but also measured ellipsometric BETA values in ranges wherein Sample System (SS) characterizing PSI and DELTA providing Transfer function, (from said ellipsometric ALPHA and ellipsometric BETA), sensitivity to noise and errors in the measurement etc. of said ellipsometric ALPHA and ellipsometric BETA, is essentially negligible, (said PSI and DELTA Transfer functions being dependent upon said measured ellipsometric ALPHA and ellipsometric ALPHA and BETA values respectively, as demonstrated in the Detailed description Section of this Disclosure by presentation of relevant Transfer Function equations). The present invention allows usably accurate and precise determination of Sample System characterizing DELTA values in regions otherwise difficult, if not impossible, for (RAE), (RPE) and (MEE) systems to, investigate, and also allows operation with a polarized light beam orientation at other than Principal or Brewster Angles. The most general use of the present invention system, then, is to allow measurement of Sample System characterizing PSI and DELTA values with uniform accuracy and precision over the full range of possibilities, (eg. (0.0<PSI<90 degrees) and (0.0<DELTA<360 degrees), with an Ellipsometer or Polarimeter and the like System which would otherwise have difficulty per forming said measurements. (For instance, where DELTA approaches zero (0.0) or one-hundred-eighty (180) degrees, (and/or perhaps the Angle of Incidence (AOI) is other than at the Brewster Angle), reflected Light from a Sample System approaches Linear Polarization and that causes BETA values to approach one (1.0), whereat DELTA transfer function, (from ALPHA and BETA), sensitivity to noise and errors in measured ALPHA and BETA become significant). The present invention, however, is also a system and method of use which allows the determination of elements in a Jones or Mueller Matrix, and determination of the "Handedness" of a polarized beam of light utilized in said Ellipsometer System. The present invention system also allows a user to easily adjust present invention system components included in a conventional Ellipsometer or Polarimeter and the like system, so that said added components are essentially end-user transparent, (see supra), at any wavelength desired, thereby negating the need to remove said added components from said present invention Ellipsometer System to allow use thereof in a conventional mode.

As alluded to in the Background Section of this Disclosure, the present invention is applicable to, for instance, essentially any type of Ellipsometer or Polarimeter and the like System in which a Rotatable or Rotating Element is present, (eq. Nulling Ellipsometer (NE), Rotatable Element Automated Nulling (REANE), Rotating Analyzer (RAE), Rotating Polarizer (RPE), Rotating Compensator (RC) and Rotating Analyzer and Polarizer Fixed Compensator (RAPFC), for instance), and/or in which a Modulator Element (ME) is present, (eg. a Modulation Element Ellipsometer (MEE)). In the directly following however, a Spectroscopic (RAE) will be used as an example. This exemplary usage is not to be interpreted as imposing any limitations on the scope of the present invention. (Note, as Jones and Mueller Matrix analysis show, computational similarities and symetries in applicable mathematics reveal that the present invention is quite general to the entire class of Rotatable Element Ellipsometers, Rotating Element Ellipsometers (REE's), Modulation Element Ellipsometers (MEE's) and Polarimeters and the like).

Continuing, a conventional Spectroscopic (RAE), such as the J.A. Woollam Co. Inc. Variable Angle Spectroscopic Ellipsometer (VASE—Registered Trademark), system is comprised of:

1. A Polarization State Generator System, (PSG), comprising:
   a. a source of a beam of light, the wavelength of which beam of light can be set as desired by a user; and
   b. a Polarizer (P) for use in setting a polarization state in said beam of light provided by said source of a beam of light.

2. A Polarization State Detector System (PSD), comprising:
   a. a Rotating Analyzer (RA), for use in processing said polarized beam of light after it interacts with a Sample System (SS), so that a linearly polarized beam of light of typically varying intensity is produced; and
   b. a Detector System (DET) for use in developing a signal from said beam of light, after it emerges from said Rotating Analyzer (RA), which signal contains information which allows determination of optical and physical properties of said Sample System (SS).

A conventional method of usage of such a Spectroscopic (RAE) system requires that the beam of light provided by the source of a beam of light be caused to pass through said Polarizer (P) to set a polarization state therein, then impinge upon the surface of a Sample System (SS) at an Angle of Incidence (AOI) which is approximately the, (wavelength dependent), Brewster Angle for said Sample System (SS). (Note that the Brewster Angle is that (AOI) at which the measured ellipsometric BETA is minimized and at which the Sample System (SS) characterizing DELTA parameter is approximately ninety (90) degrees and at which circular polarization is achieved). It is to be understood that a partial polarization state of said beam of light can be set by a user by rotation of the Polarizer (P) to set the Azimuthal Angle (POL) thereof, and also noted that each said Azimuthal Angle (POL) is associated with a specific value of the ellipsometer ellipsometric ALPHA value. It must be understood that said polarization state of said beam if light is changed by interaction with said Sample System (SS), and that the portion thereof reflected from said Sample System (SS) is caused to pass through said Rotating Analyzer (RA), thereby becoming a linearly polarized, typically varying intensity, modulated beam of light of altered polarization state, which then enters said Detector System (DET). Said Detector System (DET) serves to generate a signal from said entering beam of linearly polarized, typically varying intensity, modulated beam of light of altered polarization state, which generated signal can be subjected to Fourier Analysis, for instance, to provide measured values for ellipsometric ALPHA and ellipsometric BETA. (It is noted that ALPHA and BETA can be thought of as the signals provided by a Detector Element in an ellipsometer system).

If, in the above procedure, the Angle Of Incidence (AOI) is not set near the Brewster Angle, for the wavelength of interest, the quality of the data provided at the Detector System (DET) may be degraded. Where glass is a Sample System, as little as one-tenth (1/10) degree variance can be significant. It is also noted that in practice, an (RAE) polarized beam of light can not be set exactly to the Brewster Angle when a Sample System is a totally transparent bulk sample, like glass, because thereat PSI equals (0.0). Even application of the present invention system, ahead of a Sample System, can not avoid the fact that where PSI is zero (0.0), linearly polarized light will be reflected regardless of the polarization state of a Beam of Light impinged thereupon, although a present invention Variable Retarder placed after a Sample System might be useful in such a case. Use of a non-Brewster Angle, however, can cause PSI for such a sample to become non-zero. Hence, it would be of great utility to be able to set the Angle-of-Incidence (AOI) at essentially any value, apply a beam of light comprised of any wavelength(s), and conveniently obtain usably precise and accurate data, thereby allowing determination of Sample System (SS) characterizing PSI and DELTA values, essentially unaffected by transfer function sensitivity to noise and measurement errors in said data. The present invention enables such, in (REE's), for instance, by allowing a user to set the values of ellipsometric ALPHA and ellipsometric BETA in desired ranges.

To understand the present invention it is necessary to realize that a Birefringent Retarder can be oriented so as to effect "P" and "S" components of a polarized beam of light passing therethrough with different amounts of retardation. For instance, a linearly polarized beam of light passing through a Birefringent Retarder an be caused to become essentially circularly polarized by the effecting of an essentially ninety (90) degree retardation between one component, ( ie. "P" or "S"), relative to the other. It is also to be understood that many types of Birefringent Retarders exist. One type, termed a "zero or multiple-order-waveplate" Retarder has its Optical axis in the plane of the surface thereof. Another type, termed a "Berek-type" Retarder has its Optical axis oriented essentially perpendicular to the plane of its surface. While both identified types of Birefringent Retarders can be used in the present invention system, the Berek-type Retarder is presently preferred. The reason for this present preference has to do more with "state-of-the-art" manufacture and availability than it does with physics of operation. Presently available Berek-type Retarders simply operate better in the present invention application, and can be applied continuously over a large spectroscopic range (eg. one-hundred-ninety (190) to seventeen-Hundred (1700) namometers) and they introduce relatively less artifact content to be entered to a polarized beam of light which is passed therethrough in use. A particularly useful attribute of Berek-type Variable Retarders is that they need not be removed from an ellipsometer or polarimeter and the like system in which they are present to make them appear end-user transparent over a large range of polarized light beam wavelengths and polarized light beam (AOI's) to Sample Systems per se. A user effected "tilting" adjustment being sufficient to prevent any polarized beam of light polarization state change from being effected on said polarized beam of light passing therethrough, at any wavelength in a spectroscopic range thereof.

It is also mentioned that Babinet and Soleil Double-Wedge-type; and Kerr and Pockels effect, and Liquid Crystal, electro-optic-type; and Voigt and Cotton-Mouton Magnetic-Faraday-effect Variable Retarders which can provide Variable Retardance over a relatively large range of wavelengths, can be used in the realization of the present invention, assuming a sufficiently low artifact content is introduced to a polarized beam of light passed therethrough. These alternative Variable Retarders are better described in the Detailed Description Section of this Disclosure.

Now, as mentioned infra, it is known in the practice of Ellipsometry utilizing Rotating Analyzers, to adjust the Azimuthal Angle of a Polarizer (P) to set a measured ellipsometric ALPHA value within a desired range, regardless of investigational wavelength being utilized. In practice this is accomplished by setting a (POL) to a Sample System characterizing PSI value. However, until the present invention, it has not been possible to conveniently perform, simultaneously, a similar maneuver on a measured ellipsometric BETA value over a relatively large wavelength range, (eg. one-hundred-ninety (190) to seventeen-hundred (1700) nanometers). To provide the identified utility, the present invention teaches that at least one Variable Retarder (VR) should be placed in a Rotating Element Ellipsometer and specifically a Rotating Analyzer Ellipsometer System (RAE), (for example), between the Polarizer (P) and the Rotating Analyzer (RA), such that in use adjustment of said (VR) allows setting a measured ellipsometric BETA value within a range in which DELTA Transfer Function sensitivity to noise and errors in measurement of ellipsometric BETA is reduced or minimized. Present invention system (VR's) can be placed ahead of and/or after a Sample System (SS), within the teachings of the present invention. In use, a method of operation will then include a step in which a present Variable Retarder (VP) is adjusted to set a value of ellipsometric BETA, simultaneous with adjustment of ellipsometric ALPHA by the adjustment of a Polarizer (P), so that both ellipsometric ALPHA and ellipsometric BETA are simultaneously placed in desired ranges for optimal accuracy and precision of data. For other Rotating Element Ellipsometers, such as (RPE), (RPAFCE) etc. complimentary procedures are followed. (Note, it is to understood that a Sample System can be thought of as having an associated defining Ellipsometric PSI and DELTA regardless of the measurement system type utilized in measurement thereof, and regardless of Sample System type (eg. isotropic, anisotropic or anisotropic and depolarizing.) However, measured Ellipsometric ALPHA and Ellipsometric BETA have significance only with when a system type, (for instance, (RAE) and (RPE)) is specified, and in said context refer to signals obtained from a Detector Element therein. All systems, however, produce generally similar values which when subject to an appropriate Transfer Function, provide Sample System Characterizing PSI and DELTA values).

It should be understood that adjustment of said (VR), positioned in an Ellipsometer System as described, allows, within the range of operation of said (VR), setting an ellipsometric BETA value to near zero (0.0). This is the case whether the Angle-of-Incidence (AOI) of the polarized beam of light incident on the Sample System (SS) is set to the Brewster Angle or not. This is significant because it adds a degree of freedom to a user of an Ellipsometer System fitted with the present invention system. Said degree of freedom being the ability to utilize an (AOI) greatly removed from the Brewster Angle, and still obtain high quality, usably accurate and precise data from which accurate DELTA, (and PSI), values can be determined. Data measured at an (AOI) other than a Brewster Angle is less reliable data, but the present invention enables measurement of usably accurate and precise data in ranges of ellipsometric BETA in which, without the present invention, usable data can not be measured at all.

It is noted that it is not unknown to place Fixed or Variable Retarders between a Polarizer (P) and Rotating Analyzer (RA) in an Ellipsometer System. Variable retarders have been placed ahead of, and/or after, Sample Systems (SS) in past practice to, allow evaluation of Jones or Mueller Matrix elements.

What has not previously been demonstrated as possible, however, is the ability to adjust said so-placed (VR) components in a Spectroscopic Ellipsometer System, so as to, for instance, set measured ellipsometric BETA values over a full (0.0) to (360) degree range, and over a relatively large polarized light beam range of wavelengths, (eg. one-hundred-ninety (190) to seventeen-hundred (1700) nanometers or greater), and (AOI) range, without changing system elements.

Perhaps the reason the present invention use of a (VR) has been overlooked until now is that, as alluded to infra, most commercially available zero, and multiple-order-waveplate-type Variable Retarders are not capable of performing ellipsometric BETA value settings over a significant spectroscopic wavelength range and not introduce a significant amount of unwanted "Artifacts" on a Primary Polarized Beam of light Polarization State. In use, the presence of said Artifacts can be prohibitively difficult to compensate. (Note, Berek-type Variable Retarders, having only two surface-interfaces, produce minimal internal reflections, hence add only minimal Artifacts to a polarized beam of light passing therethrough. Artifacts are, it is noted, created by addition of the effects of internal reflections, to a primary light beam). In addition it must be understood that three typical zero-order-waveplate-type Variable Retarders (VR's) are required in series to provide a continuously variable Retardance capability over the range of zero (0.0) to ninety (90) degrees, when a wavelength range of one-hundred-ninety (190) to seventeen-hundred (1700) nanometers is covered. This is because wavelengths which are multiples of other wavelengths are present in said relatively large range of wavelengths, and if less than three such zero, or multiple-order-waveplate Variable Retarders are present, then at some wavelength, the Retardation effected thereby will become one-hundred-eighty (180) degrees, which corresponds to simply changing the orientation of a polarization component, rather than introduction of a usable retardation of an elliptical nature, to a polarized beam if light, at said wavelength. If only one such zero, or multiple-order-waveplate is utilized, it must be changed to cover a spectroscopic range. (That is, individual zero, or multiple-order-waveplates are manufactured specifically for, and applicable for use at only one wavelength). Also, if an Ellipsometer System is to be used in a mode wherein the zero, or multiple-order-waveplate-type (VF's) presence is not detectable, the zero, or multiple-order-waveplate-type (VR's) must typically be physically removed from said Ellipsometer System. This is extremely end-user inconvenient, requiring possible recalibration of the retardance each time such a retarder is introduced, and also requiring expensive and complicated connect and disconnect mounting apparatus be present in an ellipsometer system.

Continuing, the present invention preferred embodiment provides that Variable Retarder(s) utilized therein be constructed so as not to introduce undesirable Artifacts which are difficult to compensate, onto a polarized beam of light, when used to effect a retardation between quadrature components thereof. The present invention avoids the problem identified by, in the preferred embodiment, utilizing presently commercially available Berek-type (VR's), which, as mentioned infra, have only two internal reflection producing surface interfaces. Also, a Berek-type (VR), has its Optical Axis in a plane essentially perpendicular to a surface thereof. In use, instead of rotation, as is required where zero, or multiple-order-waveplate (VR's) are utilized, Berek-type Retarders are "tilted", and said "tilt" can be imposed about multiple axes, both alone and simultaneously. (Note that this would be equivalent to rotating a zero, or multiple-order-waveplate-type Retarder simultaneously in clockwise and counterclockwise directions. That is, at least two such zero, or multiple-order-waveplate-type Retarders would necessarily have to be present and in series with one another). The present invention utilizes two mutually perpendicular "tilt" axes, termed Azimuthal and Elevational by the Inventors, however other multiple axes could be selected. As mentioned infra, a very important property of said presently commercially available Berek-type (VR's) for use in Rotating Element Ellipsometers, (REE), is that a one-plate, two surface, minimal Artifact introducing, system is capable if providing retardation in the range from zero (0.0) to in excess of ninety (90) degrees over a large range of wavelengths (eg. one-hundred-ninety (190) to seventeen-hundred (1700) nanometers where a presently available J.A. Woollam Co. Inc. VASE is utilized). (A Berek-type Retarder can be oriented for use at a desired wavelength by setting a "tilt" thereof. That is, a Berek-type Retarder is not specifically manufactured for use at one wavelength, or over but a small band of wavelengths, as are typical zero or multiple-order-waveplates, but by user orientation thereof can be set so as to be useable at any wavelength, over a large range of wavelengths, emphasis added). It is emphasised however, that the present invention can be practiced utilizing other than Berek-type Variable Retarders, if said other type Variable Retarder(s) are of a quality so as not to introduce significant unwanted, difficult to compensate, Artifact content onto a polarized beam of light, simultaneous with effecting retardation between quadrature components thereof.

The present invention system then, in one preferred embodiment, adds at least one Berek-type (VR) between a Polarizer (P) and a Rotating Analyzer (RA) in a Spectroscopic Rotating Analyzer Ellipsometer to allow user control of a measured ellipsometric BETA value between one (1.0) and zero (0.0) in use. It should be appreciated that a DELTA of ninety (90) degrees is the ideal, and that corresponds to a ellipsometric BETA value of zero (0.0), but that said ideal is not an absolute requirement to improve the operation of an Ellipsometer. Any reduction in the measured value of ellipsometric BETA allows improved precision and accuracy in measured data. Rotating Element Ellipsometer Systems without the present invention are inherrantly incapable of measuring accurate DELTA Values near zero (0.0) and near one-hundred-eighty (180) degrees. As will be demonstrated in the Detailed Description Section of this Disclosure, with the present invention Berek-type (VR) present, the "quality" of measured ellipsometer BETA value data are such that DELTA's near both zero (0.0) and one-hundred-eighty (180) degrees can be more usably precisely and accurately determined therefrom. As well, as will be demonstrated in the Detailed Description Section of this Disclosure, highly precise and accurate data can be achieved where an Angle of Incidence (AOI) greatly removed from the Brewster Angle is used, (which serves to cause DELTA to approach zero (0.0) or one-hundred-eighty (180) degrees), when the present invention system is present and utilized, and this is true over a large spectroscopic range of wavelengths. (It is to be understood, however, that the present invention is not limited to application where DELTA is near zero (0.0) or one-hundred-eighty (180) degrees).

Another benefit realized by the use of presently commercially available Berek-type (VR's) is that multiaxis "tilt" capability provided thereto by the present invention system allows a user to precisely adjust the Berek-type Retarder so that a polarized beam of light passing therethrough is essentially unaffected, except for possibly a negligible attenuation, again without introducing undesired Artifacts thereonto. This allows a user to, without disassembling an Ellipsometer System and removing a present invention (VR), configure an Ellipsometer System fitted with the present invention (VR) system, as if said present invention (VR) was not present. This provides great end-user convenience in practice.

The present invention also teaches that PSI and DELTA Sample System (SS) characterizing parameters can be calculated by an indirect mathematical regression approach applied to a data set which comprises a plurality of measured ellipsometric ALPHA and ellipsometric BETA values, (or equivalents), obtained when different (VR) settings are utilized. For instance, as presented in the Detailed Description Section if this Disclosure, surprisingly successful tests have been run where two (2) Polarizer Angles (POL's) are utilized, with five (5) (VR) "Tilts" being set for each (POL), in a (RAE) System. It will be appreciated that ten (10) measured ellipsometric ALPHA-ellipsometric BETA pairs are provided by this example. It is also to be understood that any number of (POL's) and (VR) "tilts", (eg. other than the two (2) (POL's) and five (VR) "tilts" identified above), can be utilized, and be within the scope of the present invention. As well, a data set can be arrived at which corresponds any of various settings of polarized light beam wavelength and/or Angle-of-Incidence to a Sample System and/or Polarizer Angle (POL) settings and/or Variable Retarder "tilts", and use of such data in arriving at Sample System characterizing PSI and DELTA values is within the scope of the present invention.

Of course, as is well known, the presence if two (VR's) placed ahead of and after a Sample System (SS), respectively, will allow evaluation of Jones or Mueller Matrix elements.

As well, the "Handedness" of a polarized beam of light can be determined by noting the effect of a present invention (VR).

As is discussed in the Detailed Description Section of this Disclosure, the (VR) System and Method of Use of the present invention is applicable to not only Rotatable and Rotating Element Ellipsometers, (REE's), but is also applicable to Rotatable Element Nulling Ellipsometers (RENE), including automated versions (REANE) Systems, and to Modulation Element Ellipsometers, (MEE's), and to Polarimeter and the like systems. When so applied, it is mentioned at this point, that it is convenient to consider that the presence of one or more (VR's) can be thought of as forming, in combination with a Sample System, a "Composite Sample System", which Composite Sample System presents with PSI and DELTA values which the Modulation Element Ellipsometer (MEE) can measure. In the above discussion, the presence of a (VR) was described as serving to set a Polarization State in a beam of Polarized Light utilized in a (REE), which allowed measuring values of, for instance, ellipsometric ALPHA and ellipsometic BETA, in ranges in which said ellipsometric ALPHA and ellipsometric BETA transfer functions to Sample System characterizing PSI and DELTA are relatively insensitive to noise and measurement errors etc. in said ellipsometric ALPHA and ellipsometric BETA. It should be appreciated, however, that both approaches to viewing the effect of application of a (VR), (eg. serving to set a Polarization State in a Beam of Polarized Light and serving to form a "Composite Sample System" in combination with a Sample System per se.), are valid and applicable to, Rotatable Element (eg. RENE), and Rotating Element (REE) Ellipsometers, Polarimeters (P) and to Modulation Element Ellipsometer (MEE) Systems. (Note that a Sample System or a formed Composite Sample System can be isotropic, anisotropic, or anisotropic and depolarizing, which are described by a Jones Matrix, a Jones Matrix with off-diagonal elements, and a Mueller Matrix respectively. PSI and DELTA values exist for any such Sample System).

The present invention then allows formation of a Composite Sample System, said Composite Sample System being formed from a Sample System per se. by adding a Variable Retarder to an ellipsometer or polarimeter and the like system being used to investigate said Sample System per se. such that a polarized beam of light must pass through the added Variable Retarder and interact with the Sample System per se., in a series relationship with the Sample System per se. By adjustment of said Variable Retarder, the Composite Sample System can be made to present to the ellipsometer, or polarimeter and the like system with PSI and DELTA values which are in ranges which can be investigated by said ellipsometer or polarimeter etc. Other adjustable ellipsometer or polarimeter etc. elements, such as rotatable polarizer(s) and/or rotatable analyzer(s) and/or rotatable compensators can also be utilized in effecting said Composite Sample System. If the goal of a user is to measure the PSI and DELTA values of a Sample System per se., said PSI and DELTA values can be arrived at by measuring PSI and DELTA values of an effected Composite Sample System, which effected PSI and DELTA values are in ranges in which the ellipsometer or polarimeter and the like can usably accurately and precisely be utilized to measure, and then compensate (eg. subtract out), the effects of the Composite Sample System effecting Variable Retarder and any other Adjustable Elements which are present.

Present invention application to ellipsometer systems in general and to rotating polarizer and rotating analyzer systems in particular was disclosed and Claimed in Allowed patent application Ser. No. 08/422,346.

The presently Claimed version of the present invention then is, in part, a system and method of reducing the sensitivity of modulation element ellipsometer (MEE) PSI and DELTA transfer functions to measured ellipsometric parameter values which is applicable over spectroscopic range. Said method enables acquiring data from a (MEE) system which is of an accuracy and precision which allows calculation of sample system PSI and DELTA, even where other than the Brewster angle of incidence (AOI) of a polarized beam of light to a sample system is utilized, and/or even where PSI is near forty-five (45) degrees and/or DELTA is near zero, (0.0) or one-hundred-eighty (180) degrees. The method also enables determination of the "Handedness" of a beam of polarized light utilized in said (MEE).

17

Said method comprises the steps of:
1. providing a (MEE) system which in use comprises:
   a. a polarization state generator system comprising:
      1. a source of a beam of light;
      2. a means for setting a polarization state in said beam of light;
   b. a polarized beam modulation element;
   c. a sample system; and
   d. a polarization state detector system comprising:
      1. an analyzer; and
      2. a detector system;
where said polarized beam modulation element is positioned at a location selected from the group consisting of: (before and after said sample system).

Said (MEE) further comprises, in the preferred embodiment, at least one Berek-type variable retarder placed between said polarization state generator system, and said polarization state detector system. During use a beam of light is caused to exit said source of a beam of light, and have an ellipsometric parameter determining state of polarization effected therein by said means for setting a polarization state. Said polarized beam of light is caused to interact with said sample system, and with said polarized beam modulation element, and with said at least one Berek-type variable retarder placed between said polarization state generator system and said polarization state detector system. Of particular importance is that the polarization state generator system can be adjusted to set a value of a first ellipsometric parameter and said at least one Berek-type variable retarder can be tilted, so as to set a value of a second ellipsometric parameter, such that said first and second ellipsometric parameters are in ranges in which a transfer function which mediates determining DELTA from said measured ellipsometric first and second parameters is relatively immune to noise and errors in measurement etc. of said ellipsometric first and second parameters.

Said method continues by causing a beam of light to exit said source of a beam of light, and causing an ellipsometric first parameter setting state of polarization other with said means for setting a polarization state; then causing said resulting polarized beam of light to interact with said sample system, and with said polarized beam modulation element, and with said at least one Berek-type variable retarder placed between said polarization state generator system and said polarization state detector system. With said means for setting a state of polarization being adjusted to at least one setting and said at least one Berek-type variable retarder being adjusted to, sequentially, a plurality of tilt settings, ellipsometric first and ellipsometric second parameter values data are obtained and PSI and DELTA values are determined and utilizing by a mathematical technique that compensates adjustments made to said means for setting a state of polarization and said at least one Berek-type variable retarder on measured ellipsometric first and ellipsometric second parameter values.

Alternative embodiments add or replace said at least one Berek-type retarder with least one variable retarder selected from the group consisting of:
   a. a system of at least two fixed-order-waveplate-type retarders which can be rotated with respect to one another, each about an axis perpendicular to an optical axes thereof, said optical axes being parallel to the surface of said fixed-order-waveplate-type retarders;
   b. a Babinet dual wedge-type variable retarder;
   c. a Soleil dual wedge-type variable retarder;
   d. a Kerr electro-optical-type variable retarder;

18 e. a Pockels electro-optical-type variable retarder;
   f. a liquid crystal electro-optical-type variable retarder;
   g. a Voigt magnetic-faraday-effect variable retarder; and
   h. a Cotton-Mouton magnetic-faraday-effect variable retarder.

Where said (MEE) comprises at least one Berek-type variable retarder placed between said polarization state generator system, and said polarization state detector system said at least one Berek-type variable retarder can be tilted so as to set a value of an ellipsometric second parameter in a range in which a transfer function which mediates determining DELTA from a measured ellipsometric first parameter and ellipsometric second parameter values is relatively immune to noise and errors in measurement etc. of said ellipsometric second parameter. Where other types of retarders, (than Berek), are present rotation or sliding of elements with respect to one another etc. replace tilting as a means of setting retardation.

Said (MEE) is comprised of computational means which perform said determination of said sample system PSI and DELTA, said determination of said sample system PSI and DELTA requiring input of data acquired with said ellipsometric second ellipsometric parameter value setting Berek-type variable retarder set in a plurality of tilt positions, which computational means compensate acquired data input thereto, for the effects of said required plurality of ellipsometric second parameter setting Berek-type variable retarder tilts.

Said modulation element ellipsometer (MEE) system an have the Berek-type variable retarder mounted so as to simultaneously allow user directed tilt in more than one direction, said multiple tilt capability alllowing a user to adjust said Berek-type retarder so that it has no effect, other than a negligible attenuation, on a beam of polarized light passing therethrough.

A present invention (MEE) system can further comprise at least one additional element selected from the group consisting of:
   a. a stationary polarizer;
   b. a stationary analyzer;
   c. a stationary compensator;
   d. a rotating polarizer; and
   e. a rotating analyzer.

Said method of determining sample system PSI and DELTA values by use of a modulation element ellipsometer (MEE) system, can comprise the steps of:
   a. measuring a plurality of sample system ellipsometric first and ellipsometric second parameter pairs, as a function of at least one means for setting a polarization state in said beam of light setting(s), and a plurality of variable retarder settings; and
   b. applying a mathematical technique to said plurality of measured ellipsometric first and ellipsometric second parameter pairs to determine PSI and DELTA values for said sample system per se. while compensating for the presence of said variable retarder.

Said method of determining sample system PSI and DELTA values by use of a modulation element ellipsometer (MEE) system, can comprise the steps of:
   a. measuring a plurality of sample system ellipsometric first and ellipsometric second parameter pairs corresponding to, at each of at least one means for setting a polarization state in said beam of light setting(s), at least five Berek-type retarder settings, said Berek-type retarder settings including no-tilt, clockwise and counterclockwise elevational, and clockwise and counterclockwise azimuthal tilts; and b. applying a mathematical technique to said plurality of measured ellipsometric first and ellipsometric second parameter pairs to determine sample system PSI and DELTA values, while compensating for presence of said at least one Berek-type variable retarder.

Where other than Berek-type retarders are utilized, said method of determining sample system PSI and DELTA values by use of a modulation element ellipsometer (MEE) system, can also comprise the steps of:

a. measuring a plurality of sample system ellipsometric first and ellipsometric second parameter pairs as a function of at least one means for setting a polarization state in said beam of light setting(s), and a plurality of variable retarder settings; and b. applying a mathematical technique to said plurality of measured ellipsometric first and ellipsometric second parameter pairs to determine sample system PSI and DELTA values, while compensating for the presence of said at least one variable retarder.

The present invention can also be described as a modulation element ellipsometer (MEE) system which enables accurate and precise determination of PSI and DELTA values of essentially any investigatable sample system. In which said modulation element ellipsometer (MEE) system there is present a means for setting at least one polarization state in a beam of polarized light and means for identifying, and means for monitoring, a polarization state in said polarized beam of light, after an interaction thereof with a sample system. Between said means for setting at least one polarization state in a beam of polarized light and said means for monitoring a polarization state in said polarized beam of light, there is present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle. Said obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometric data, as said modulation element ellipsometer (MEE) system further comprises a computational means which performs determination of investigated sample system PSI and DELTA values, utilizing data obtained with said at least one adjustable means for controlling ellipsometric phase angle between orthogonal components in a polarized beam of light, being set to at least two selected settings. Said computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values.

In said modulation element ellipsometer system at least one selection from the group consisting of: (said means for setting at least one polarization state and said means for identifying a polarization state in said polarized beam of light), is an adjustable means for controlling an ellipsometric relative magnitude ratio of said orthogonal components, such that a plurality of ellipsometric relative magnitude ratios of said orthogonal components can be set thereby. In use, said computational means further performs compensation of any effects on obtained data resulting from adjustment(s) entered to ellipsometric relative magnitude ratios of said orthogonal components by said adjustable means for controlling an ellipsometric relative magnitude ratio of said orthogonal components in a polarized beam of light which is caused to interact with a sample system.

In said modulation element ellipsometer (MEE) system said at least one adjustable means for controlling an ellipsometric phase angle between said orthogonal components in a polarized beam of light comprises a variable retarder, and said adjustable means for controlling an ellipsometric relative magnitude ratio of orthogonal components in a polarized beam of light comprises an adjustable polarizer and/or an adjustable analyzer which preferably operate over a spectroscopic range of at least two-hundred-thirty (230) to seventeen-hundred (1700) nanometers.

As mentioned said present invention modulation element ellipsometer (MEE) system can include a Berek-type variable retarder with its optical axis directed essentially perpendicular to a surface thereof. Said Berek-type variable retarder can be mounted in said ellipsometer system so as to allow it to be tilted about multiple axes thereby enabling it to provide variable amounts of retardance between orthogonal components in a beam of polarized light caused to pass therethrough, and so that optical axis can be caused to be aligned with said polarized beam of light with the results being that said Berek-type variable retarder becomes essentially end-user "transparent", without removal of said Berek-type variable retarder from said ellipsometer system.

Also as mentioned said variable retarder in said modulation element ellipsometer (MEE) system can be selected from the group consisting of:

a. a system of at least two fixed-order-waveplate-type retarders which can be rotated with respect to one another, each about an axis perpendicular to an optical axes thereof, said optical axes being parallel to the surface of said fixed-order-waveplate-type retarders;

b. a Babinet dual wedge-type variable retarder;

c. a Soleil dual wedge-type variable retarder;

d. a Kerr electro-optical-type variable retarder;

e. a Pockels electro-optical-type variable retarder;

f. a liquid crystal electro-optical-type variable retarder;

g. a Voigt magnetic-faraday-effect variable retarder; and h. a Cotton-Mouton magnetic-faraday-effect variable retarder.

A general method of determination of sample system PSI and DELTA value with improved accuracy and precision comprising, in a functional order, can comprise the steps of:

a. providing a modulation element ellipsometer (MEE) system which enables accurate and precise determination of PSI and DELTA values of essentially any investigatable sample system;

said modulation element ellipsometer (MEE) system comprising means for setting at least one polarization state in a beam of polarized light and means for identifying, and means for monitoring, a polarization state in said polarized beam of light, after an interaction thereof with a sample system;

between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometic data;

said modulation element ellipsometer (MEE) system being further comprised of computational means which performs determination of investigated sample system PSI and DELTA values, which computational means utilizes data obtained with said at least one adjustable means for controlling ellipsometric phase angle between orthogonal components in a polarized beam of light, being set to at least two selected settings, and which computational means performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values;

b. placing a sample system to be investigated into said modulation element (MEE) ellipsometer system and causing a beam of polarized light from said means for setting at least one polarization state in a beam of polarized light to interact therewith and enter said means for monitoring a polarization state;

c. adjusting said at least one adjustable means for controlling ellipsometric phase angle between said orthogonal components to be sequentially set to a plurality of settings while ellipsometric data is obtained by said means for monitoring a polarization state in said polarized beam of light at at least two selected settings from said plurality settings of said at least one adjustable means for controlling a value of ellipsometric phase angle between said orthogonal components;

d. causing said computational means to determine investigated sample system PSI and DELTA values by a method which performs compensation of the effects of said at least one adjustable means for controlling ellipsometric phase angle between orthogonal components in a polarized beam of light on said ellipsometric data obtained at said at least two selected settings of said at least one adjustable means for controlling ellipsometric phase angle between orthogonal components in a polarized beam of light which is caused to interact with a sample system, in determining sample system PSI and DELTA values; and e. optionally determining at least some of members of the group consisting of: (the "Handedness", Stores Vector, and Jones and Mueller Matrix components) of said polarized beam of light and investigated sample system.

Said method of determination of sample system PSI and DELTA values can comprise obtaining a plurality of relative magnitude ratios of orthogonal components and phase angles between orthogonal components are obtained, at least some of which plurality of ellipsometric relative magnitude ratios of orthogonal components and measured ellipsometric phase angles between orthogonal components correspond to sequential adjusted settings of ellipsometric relative magnitude ratios of orthogonal components present in said beam of polarized light, said sequential adjusted settings being effected by adjustment of at least one member of the group consisting of: (said means for setting at least one polarization state in a beam of polarized light and said means for identifying a polarization state in said polarized beam of light ); and in which said computational means is also caused to perform compensation of the effects of said sequential adjusted settings of ellipsometric relative magnitude ratios of orthogonal components present in said beam of polarized light which is caused by said modulation element ellipsometer (MEE) system to interact with a sample system, in determining investigated sample system PSI and DELTA values.

In addition, said method of determination of sample system PSI and DELTA values can comprise obtaining a plurality of ellipsometric phase angles between orthogonal components are effected at each sequential adjusted setting of ellipsometric relative magnitude ratio of orthogonal components present in said beam of polarized light which is caused by said modulation element ellipsometer (MEE) system to interact with a sample system.

The present invention will be better understood by reference to the Detailed Description Section of this Disclosure, with reference to the Drawings.

SUMMARY OF THE INVENTION

It is a primary purpose of the present invention system and method of application thereof, to provide a means by which the polarization state of a beam of light in, for instance, a Spectroscopic Ellipsometer or Polarimeter and the like System, can be controlled so that the sensitivity of a monitoring polarization state detector to noise and measurement errors etc. therein, is decreased.

It is further a primary purpose of the present invention to provide a system for controlling the polarization state of a polarized beam of light in, for instance, an Ellipsometer or Polarimeter and the like System, such that a measured ellipsometric magnitude ratio of quadrature (hereinafter assumed as "P" and "S" components for nonlimiting purposes of discussion), components, and a measured ellipsometric phase angle between said "P" and "S" components are simultaneously set within ranges in which a Polarization State Detector System has improved measurement capability and reduced sensitivity to noise and errors in the measurement, such that Sample System PSI and DELTA defining parameters can be more usably accurately and precisely determined from said measured ellipsometric ratio of "P" and "S" components, and measured ellipsometric phase angle between said "P" and "S" components. Alternatively viewed, the present invention system allows formation of a "Composite Sample System", in conjunction with a Sample System per se., the PSI and DELTA of which Composite Sample System are in ranges in which they can be usably accurately and precisely measured by an ellipsometer or polarimeter and the like system, to allow the PSI and DELTA of said Sample System per se. to be found by compensating (eg. subtracting out), for the effects of said present invention system.

It is another purpose of the present invention to provide Rotating Element Ellipsometers with a system providing users the capability of setting not only ellipsometric ALPHA, but also ellipsometric BETA values within desired ranges, such that determination of PSI and DELTA Sample System characterizing values, (obtained by direct application of transfer functions to measured ellipsometric ALPHA and ellipsometric BETA values, or by indirect mathematical regression applied to an array of measured ellipsometric ALPHA and ellipsometric BETA data pair values), sensitivity to noise and errors in measurement etc. of said ellipsometric ALPHA and ellipsometric BETA is minimized, thereby allowing determination of DELTA values over the entire range of zero (0.0) to three-hundred-sixty (360) degrees, and in particular in ranges otherwise difficult or impossible to investigate, (ie. near zero (0.0) and near one-hundred-eighty (180) degrees).

It is an additional purpose of the present invention to provide Rotatable Element, Rotating Element and Modulation Element Ellipsometers, (and similarly designated Polarimeter and the like Systems), with a system which provides users thereof the capability of forming a "Composite Sample System", comprised of a Sample System per se. in series with a Variable Retarder, which "Composite Sample System" presents with PSI and DELTA values which are in ranges which can be usably accurately and precisely measured, and in which sensitivity to noise and measurement errors is decreased, so that Sample System per se. PSI and DELTA values can be found from said measured PSI and DELTA values by compensating for, (eg. subtracting out), the effects of the presence of said Variable Retarder.

It is still yet another purpose of the present invention to teach that presently commercially available Berek-type Variable Retarder(s), (which have their Optical Axis perpendicular to a surface thereof), should be mounted so as to enable multiple axes of "tilt" rotation, around which multiple axes a user can control rotation, such that a Berek-type Variable Retarder added to an Ellipsometer or Polarimeter and the like System can be tilted around said multiple axes as necessary to essentially eliminate effects of its presence, such that it does not modify a polarized beam of light which passes therethrough during use, other than by causing an essentially negligible attenuation therein, as opposed to changing a state of polarization thereof.

It is yet still another purpose of the present invention to teach that presently commercially available systems of multiple zero-order, or multple-higher-order-waveplate-type Retarders in series, as well as Babinet and/or Soleil-type Variable Retarder(s), and/or electro-optical-effect-type Kerr and/or Pockel and/or Liquid Crystal Variable Retarder(s), and/or magnetic-Faraday-effect Voigt and/or Cotton-Mouton Retarder(s) can be mounted in Rotating Element Ellipsometer or Polarimeter and the like Systems so as to enable modification of a State of Polarization in a beam of polarized light which passes therethrough during use, for the same purposes as described with respect to the Berek-type Variable retarder.

It is another purpose of the present invention to teach that addition of a system which allows setting a measured ellipsometric BETA value within a user desired range, allows operation of a Rotatable Element, Rotating Element or Modulation Element Ellipsometer or Polarimeter and the like System, at Angles of Incidence, (of a Polarized Beam of Light with respect to a Sample System), other than the Principal or Brewster Angle, while enabling the gathering of useably precise and accurate data from which can be calculated PSI and DELTA Sample System characterizing parameters.

It is yet still another purpose of the present invention to teach a system for meeting the above recited purposes which is spectroscopic, and which can be used with Sample System investigating polarized beams of light over a relatively large range of wavelengths, (eg. one-hundred-ninety (190) to seventeen-hundred (1700) nanometers), which system requires only user adjustment of polarized light beam polarization state affecting elements to accomodate various wavelengths, rather than change of such Ellipsometer or Polarimeter and the like System Elements.

It is still yet another purpose of the present invention to provide a system which can be utilized to determine elements of a Jones or Mueller Matrix in Ellipsometer or Polarimeter and the like Systems, including over a wide spectral range.

It is another purpose of the present invention to teach a system which can be utilized to determine the "Handedness" of a polarized beam of light in Ellipsometer or Polarimeter and the like Systems, including over a wide spectral range, where handedness can depend on wavelength.

It is still another purpose of the present invention to meet the above stated purposes by addition of elements to Ellipsometer or Polarimeter and the like Systems which can be user adjusted to appear end-user "Transparent" when desired, without any disassembly of, or removal of elements from said Ellipsometer or Polarimeter and the like Systems.

It is additionally a purpose of the present invention to teach methods of use of Ellipsometer and Polarimeter and the like Systems, to which a system of the present invention has been added, which methods of use allow above cited purposes associated with use of a system of the present invention, to be achieved.

DETAILED DESCRIPTION

Figure 1:
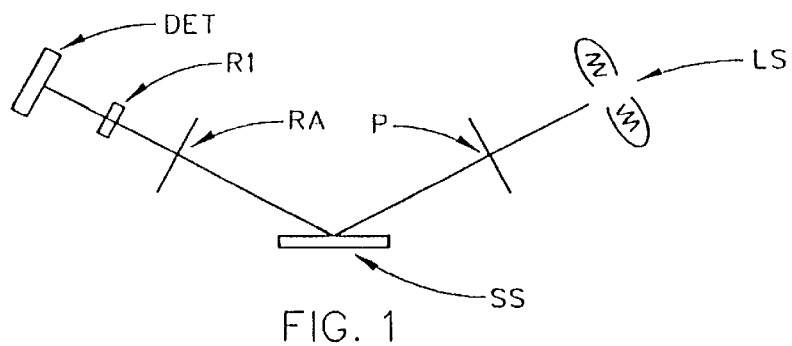
FIG. 1 shows a Variable Angle Spectroscopic Ellipsometer (VASE—Registered Trademark), System.

The present invention system and method of use can be applied to essentially any Ellipsometer or Polarimeter and the like System, which contains one or more Rotatable or Rotating Elements, and/or which contains Polarization State Modulation Elements.

The present invention is a system and method of use for controlling the polarization state of a polarized beam of light utilized in, for instance, a Spectroscopic Ellipsometer (SE) system. The present invention system and method of use allows one to simultaneously set a measured ellipsometric relative magnitude ratio of orthogonal, (hereinafter assumed as "P" and "S" components as a nonlimiting example thereof), components, as well as a measured ellipsometric phase angle between said orthogonal "P" and "S" components in a polarized beam of light. (Note that the "P" component is that component of a polarized beam of light in a plane defined by a normal to a Sample System surface, and the incident and reflected or transmitted beams, while the "S" component is perpendicular thereto and parallel to the surface of the Sample System). The purpose of controlling said polarization state of said polarized beam of light is to cause said measured ellipsometric relative magnitude ratio of "P" and "S" components, and said measured retardation phase angle between said "P" and "S" components to be in ranges in which a Sample System characterizing PSI and DELTA monitoring Polarization State Detector demonstrates decreased sensitivity to noise and errors in measurement etc. thereof. When combined with compensating for, (eg. subtracting out or otherwise), the influence of the presence of the present invention system on measured PSI and DELTA values, said present invention system and method of use, allows accurate sensitive measurement of Sample System Characterizing PSI and DELTA values, in ranges otherwise difficult, of not impossible, to investigate. This is accomplished by enabling measurement of PSI and DELTA values, or parameters determinative thereof, in ranges in which they are not sensitive to noise and measurement errors. For instance, use of the present invention allows usably accurate and precise Sample System characterizing DELTA values to be determined near zero (0.0) and one-hundred-eighty (180) degrees in Rotating Analyzer Ellipsometer (RAE), Rotating Polarizer (RPE), and Modulation Element Ellipsometers (MEE's), and accurate PSI values near Forty-five (45) degrees can also be determined in (MEE's). As well, Angles of Incidence (AOI's) far removed from a "Brewster", (alternatively termed the "Principal Angle"), can be utilized and accurate values of PSI and DELTA determined, when the present invention system and method are practiced.

(Note that "P" and "S" components and PSI and DELTA are defined and derived in the Text titled "ELLIPSOMETRY AND POLARIZED LIGHT", By Azzam and Bashara, North-Holland, 1977, which text is incorporated by reference in this Disclosure).

As a specific example, the J.A. Woollam Co., Inc. Variable Angle Spectroscopic Ellipsometer (VASE—Registered Trademark), allows application of a Polarized Beam of Light of One (1) Wavelength at a time to a Sample System (SS), at one Angle of Incidence (AOI) at a time. In use, various (AOI's) are utilized, as are various Wavelengths at said various (AOI's), to acquire a Data Set, use of which allows calculation of Sample System PSI and DELTA Characterizing parameter Constant Values. (Note that while different PSI and DELTA Constant Values are associated with different (AOI) and Wavelengths, PSI and DELTA are Sample System characterizing parameters). In addition, note that typical technique requires that an Angle of Incidence (AOI) near an optimum (AOI), (termed the Brewster Angle, or Principal (AOI), see supra), be utilized with a Sample System under investigation, to assure the acquisition of a Data Set which is of a precision and accuracy that allows reliable calculation of Sample System (SS) characterizing PSI, and especially DELTA, Constant Values therefrom. Depending upon the Sample System being investigated, deviations from the Brewster Angle can be permissible, but where, for instance, glass is investigated, said tolerable deviation might be as small as one-tenth (1/10) a degree. (It is noted that operation cat the Brewster (AOI) is always preferable because errors in data acquisition thereat are minimized. That is, data acquired using a Brewster Angle (AOI) is accurate within tighter plus/minus "confidence limits". However, even though the possible error in data acquired at a non-Brewster (AOI) is less than optimum, the present invention makes possible the acquistion of "useably accurate and precise" data at non-Brewster (AOI's), which without the present invention could not be measured. The confidence related to the accuracy of said usably accurate and precise data is not as high as if the data were acquired using a Brewster Angle (AOI), but the data can none-the-less be measured with "usable" accuracy and precision when the present invention is applied, where measurement thereof without application of the present invention, would prevent measurement of "usable" data at a non-Brewster Angle (AOI)).

In addition, the J.A. Woollam Co. manufactures M-44, and M-88 etc. Rotating Analyzer Ellipsometer (RAE) Systems which allow simultaneously application and analysis of a multiplicity (eg. forty-four (44) or eighty-eight (88) etc.), of Wavelengths in a Polarized Beam of Light. While the present invention was developed utilizing a (VASE) System, it can in some instances also be applied to the M-44 and M-88 etc. systems. One said instance involves in-situ-real-time data acquisition from Sample System (SS) processing systems in which an Ellipsometer System can not be interfaced to said processing system in a manner which allows a beam of polarized light from said Ellipsometer System to impinge upon said Sample System (SS) at near the ideal, well known, Brewster Angle, or Principal Angle of Incidence (AOI).

Continuing, Ellipsometers, (Rotating Analyzer Ellipsometer (RAE) Systems being used as an example herein), operate by detecting the change in Polarization State caused in a Beam of Polarized Light, when said Beam of Polarized Light is caused to interact with a Sample System (SS).

Briefly, as shown in FIG. 1, for reference purposes, a basic J.A. Woollam Co. Rotating Analyzer Ellipsometer (RAE) VASE System comprises:

1. A Polarization State Generator System (PSG) comprising:
   a. a Source of a Beam of Light, which Beam of Light can typically comprises a multiplicity of wavelengths, which wavelengths are utilized one at a time;
   b. a Polarizer (P) which serves to set a state of polarization in said beam of light by adjustment of the Polarizer Angle (POL) thereof;
   c. a Means for causing said Polarized Beam of Light to interact with a Sample System, (ie. a means to set an Angle of Incidence (AOI).
2. A Polarization State detector System (PSD) comprising:
   a. a Rotating Analyzer (RA) which serves to process said Polarized Beam of Light after it interacts with said Sample System (SS), such that a typically Modulated Intensity, essentially Linearly Polarized Beam of Light, is produced;
   b. a Detector System (DET) which measures the Intensity waveform of said resulting Elliptically Polarized typically Modulated Intensity waveform as a function of time.

(Note, a Retarder (R1) is also shown as present in FIG. 1. Said Retarder (R1) is typically not present in a J.A. Woollam Co. Inc. (RAE) VASE Ellipsometer system, and is discussed for information purposes only supra, with regard to the J.A. Woollam Co. Inc. M-44, and M-88 (RAE) Ellipsometer Systems in which said (R1) Retarder is commonly employed. Said M44 and M88 (RAE) Ellipsometer Systems provide for a Polarized Beam of Light leaving a Sample System to enter a Detector Element (DE) after passing through a Rotating Analyzer (RA), without any focusing being provided).

It is to be understood then that an Ellipsometer System, in use, can be considered to be comprised of a Polarization State Generator System, (PSG), and a Polarization State Detector System, (PSD), with a Sample System (SS) placed therebetween, where all components preceding the Sample System (SS) are lumped together under the term "Polarization State Generator System (PSG)" and all components after the Sample System (SS) are lumped together under the term "Polarization State Detector System (PSD)". Thus, in the above recitation, Components identified as 1a, 1b and 1c are considered to be part of the (PSG) and the Components identified in 2a and 2b are considered to be part of the (PSD).

Next, it is to be understood that the intensity waveform of an elliptically polarized beam of light entering a Rotating Analyzer Ellipsometer (RAE) Detector System (DET), as a function of time, is characterized by a mathematical equation which involves well known measurable Ellipsometric ALPHA and BETA parameters in a trigonometric relationship, with the Azmuthal Angle of said Rotating Analyzer being the argument of said trigonometric functions. See EQ. 1. Equation 1 provides definitions for ellipsometric ALPHA and BETA.

$$I=IO*(I+ALPHA* COS (ANL)+BETA* SIN (ANL)); \quad EQ. 1$$

where "ANL" is the Rotating Analyzer Azimuth Angle. (Note that EQ. 1 also applies to a Rotating Polarizer Ellipsometer wherein the angle "ANL" is replaced with a similar angle "POL" which corresponds to a Rotating Polarizer Azimuth Angle. Also EQ. 1 is an "ideal" equation. In practice ALPHA and BETA are extracted from measured signals after application of calibration constants not discussed herein).

(It is to be noted that EQ. 1 can be satisfied by any number of ellipsometric ALPHA and ellipsometric BETA value pairs. That is, there is not but a single unique pair of ellipsometric ALPHA and ellipsometric BETA values which satisfy EQ. 1. If, for instance, one arbitrarily sets an ellipsometric ALPHA value, (which can be accomplished by adjusting the Polarizer (P) Polarization Angle (POL) by a adjustment of said Polarizer in said (PSG)), evaluation of EQ. 1 in view of a Detector provided set of Data will provide an accompanying ellipsometric BETA value, but such an ellipsometric ALPHA-BETA pair will exist for each (POL) setting a user cares to set).

While not a principal focus of the present invention, previous activity by the J.A. Woollam Co. has determined that for their "M-44" and M-88" (RAE's) the Retarder (R1) identified in FIG. 1 is best be placed after the Rotating Analyzer and ahead of the Detector System (DET) so that, during use, an essentially linearly polarized beam of light which emerges from the Rotating Analyzer, after leaving the Sample System (SS), (without any focusing being applied), is converted to an elliptically polarized beam of light, (ideally a circularly polarized beam of light), prior to entry to said Detector. (Note, unpolarized light can also be utilized with success). Again, this is because most Detectors, (in a Polarization State Detector System (PSD)), are less prone to introduce Polarization Dependent Sensitivity errors into Polarized Light Beam Intensity measurements when an entering polarized beam of light is elliptically, (preferably essentially circularly), polarized than when it is linearly polarized. (Note that circular polarization refers to the state wherein the well known "P" (parallel to a plane of incidence defined by a perpendicular to an investigated sample system surface and the incident and reflected or transmitted beam (s)), and "S" (parallel to the surface of said sample system and perpendicular to said "P" component), components of a polarized beam of light are at ninety degrees with respect to one another, and linear polarization refers to a state in which said "P" and "S" components are in phase. It is noted also that when referring to a Beam of light entering a Detector Element (DE), it is often convenient to adopt a reference coordinate system with respect to said Detector Element, rather than a Sample System). Particularly where a Diffraction Grating is present in a Detector System, (but not limited to said case), it has been found that Detector Polarization Dependence Sensitivity of a Detector can be greatly reduced by application of an essentially circularly polarized Beam of Light thereto, as compared to the result when a linearly polarized beam of light is so applied. Previous Patent Applications (eg. Ser. Nos. 08/265,325 and 08/339,834), submitted by the J.A. Woollam Co. focus on this use of Retarders in a Rotating Analyzer Ellipsometer system. (Note, if multiple wavelengths are utilized, said Retarder might be Variable to allow an optimum Retardance to be set for each as it is utilized, but in general, for the purposes of this Disclosure, said Retarder for minimizing Detector polarization dependent sensitivity can be considered as Fixed).

Now, the present invention, in its preferred embodiment, makes use of one or more Retarder(s), (eg. Variable Retarder (s)), (see FIG. 2 (VR1) & (VR2)), but for a very different purpose and in a very different manner than as discussed with respect to Retarder (R1).

It is to be understood that a Variable Retarder can be applied in a system in such a way that the amount of Retardation provided thereby is Continuously Variable. That is, a Variable Retarder can be oriented in a system so as to have essentially no effect on a polarized beam of light passing therethrough, (other than perhaps an essentially negligible minor essentially linear attenuation effect on the intensity thereof), or it can be oriented in a system to effectively convert linear polarization to essentially circular polarization, (that is, provide ninety (90) degrees of Retardation to the "P" relative to the "S" component in a polarized beam of light and vice versa), or it can provide other amounts of Retardation, greater or lesser than Ninety (90) degrees. For instance, a Berek-Type Variable Retarder, (see supra), can be placed in an Ellipsometer System and positioned such that a polarized beam of light has an angle of incidence (AOI) of zero (0.0) degrees to the Optical Axis thereof, (which Optical Axis is, ideally, perpendicular to the surfaces of said Berek-Type Variable Retarder), so that the polarization state of said polarized beam of light is not effected by the presence of said Berek-type Retarder. However, if the Berek-Type Variable Retarder is "Tilted" so that the Beam of polarized light has an angle of incidence (AOI) other than zero (0.0) degrees to the Optical Axis thereof, the polarization state, (ie. the angular relationship of the "P" and "S" components with respect to one another), of said polarized beam of light can be greatly effected. Greater angles of "Tilt" will effect an impinging polarized beam of light with effectively greater retardation. It is noted that a Berek-Type Variable Retarder can provide continuously variable amounts of Retardation in excess of the range of zero (0.0) to ninety (90) degrees, over a large range of wavelengths as well. That is, unlike individual zero and multiple-order-waveplates with optical axes in a plane parallel to a surface thereof, Berek-type Retarders are not designed for use at but a single wavelength, (or at best a small (eg. perhaps one-hundred (100) nanometers), band of wavelengths around an average design-wavelength). This makes said Berek-type Retarders especially attractive in the context of the present invention. It is also noted that while capable of operating over a large wavelength range, a Berek-type Variable Retarder has only two surface-interfaces which can serve to internally reflect an impinging polarized beam of light. As a result, minimal Artifacts are added to a polarized beam of light by passage therethrough. Because of this, typically available Berek-type Variable Retarders are preferred in the embodiment of the present invention.

Figure 4A:
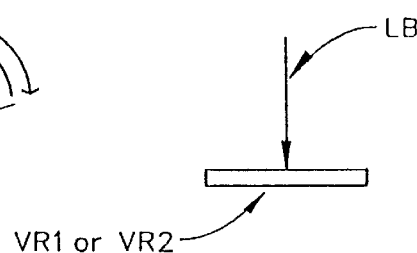
FIG. 4a shows a Retarder with a light beam incident thereon perpendicular to the surface thereof.
Figure 4B:
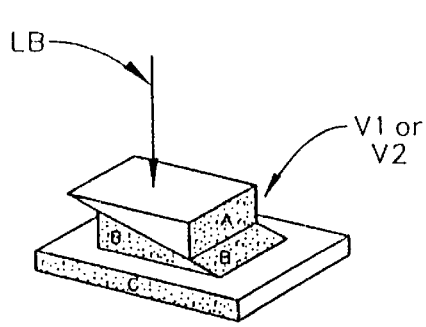
FIG. 4b shows Babinet and Soleil-type Variable Retarder Systems.
Figure 4C:
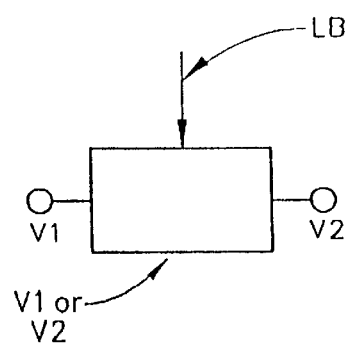
FIG. 4c indicates electro-optical-effect Kerr, Pockel and Liquid Crystal-type Variable Retarders, as well as magnetic-Faraday-effect Voigt and Cotton-Mouton-type Retarders.

In addition to Berek-type Variable Retarders, it is also possible to utilize Liquid Crystal, Kerr, Pockels, Babinet and Soleil Variable Retarders and systems of multiple seriesed zero, or multiple-order-waveplate-type Retarders, (see supra) as Variable Retarders. Said various types of Variable Retarders are well known by those skilled in the art of Ellipsometry, and will be but briefly described herein. First, Liquid Crystal Variable Retarders are true zero-order retarders in which the Retardance effected on a polarized beam of light changes with a voltage applied thereto. Next, Kerr and Pockels Variable Retarders are both electro-optical-type Variable Retarders which change Birefringence when an electric field is applied thereto. FIG. 4c provides representation of Kerr, Pockel and Liquid Crystal Variable Retarders generally. (Note it is not primarily a geometrical shape which serves as a Kerr, Pockel and Liquid Crystal Variable Retarders basis of operation, but rather the effects the application of electrical fields and voltages exert on the birefringence nature of materials from which they are constructed, hence the rather simple representation of FIG. 4c). Induced Birefringence is proportional to the square, and linearly, to applied Electric fields in Kerr and Pockels Variable Retarders, respectively. Also available are Variable Retarders which operate based upon application of a magnetic field. FIG. 4c is again used as a representation thereof, where V1 and V2 are considered to be an applied Magnetic Field. Examples of such "magnetic-Faraday-effect" Variable Retarders are Voigt and Cotton-Mouton systems. Said Variable Retarders provide Birefringence proportional to the square of an applied magnetic field. Continuing, Babinet and Soleil Variable Retarders are each comprised of two wedges, the angled faces of which are placed into slidable contact with one another. As said wedges are caused to move with respect to one another, the effective thickness encountered by a beam of light passing therethrough at a fixed location with respect thereto changes. Said change in effective thickness changes the amount of birefringent retardation effected thereby. Reference to FIG. 4b demonstrates that Soleil Variable Retarders also have an essentially nonvariable Retarder in series with the two-wedge Variable Retarder system. The Optical axes, (eg. (A) and (B)), of the two wedges in a Babinet Variable Retarder are typically oriented at ninety (90) degrees with respect to one another, while in a Soleil Variable retarder said optical axes are oriented in-line with one another, (eg. (A) and (B')), while the essentially nonvariable Retarder optical axis (C) is oriented at ninety (90) degrees with respect thereto. The above identified alternative Variable Retarders are well known and can be applied to the present invention in addition to Berek-type and multiple zero, or multiple-order-waveplate-type Retarder Systems. The criteria for application being that a Variable Retarder can be made operable over a relatively large range of wavelengths, (eg. they are usable in a spectroscopic ellipsometer system which operates over, for instance, the range of one-hundred-ninety (190) to seventeen-hundred (1700) nanometers or greater), and that significant Artifact content, which can be prohibitively difficult to compensate out, is not contributed to a polarized beam of light by interaction therewith. It is also to be understood that the terminology, (eg. Berek, Babinet, Soleil, Kerr, Pockels, Liquid Crystal, Voigt and Cotton-Mouton etc.) is to be interpreted broadly rather than limiting, to Variable Retarders which operate functionally as described. That is, Berek refers to Variable Retarders with an optical axis perpendicular to the surface thereof, while zero, or multiple-order-waveplate Variable Retarders refer to those with an optical axis parallel to the surface thereof. Babinet and Soleil are to be interpreted as identifying any Variable Retarders of dual wedge construction. Kerr, Pockels and Liquid Crystal are to be interpreted to identify any Variable Retarders which operate based upon electro-optical effects and Voigt and Cotton-Mouton are terms which are to be interpreted to identify any Variable Retarders which operate based upon magnetic-optic-effects. FIGS. 4a, 4b and 4c each show a Light Beam (LB) impinging thereon. It is also noted that a plurality of Variable Retarders can be utilized in an ellipsometer or polarimeter and the like system, perhaps one prior to and one after a Sample System, and that said Variable Retarders can be of similar or different types.

Regarding Rotating Analyzer Ellipsometers (RAE's), it is to be understood that well known practice is to determine ellipsometric ALPHA and ellipsometric BETA as defined in EQ. 1, in view of a Detector System (DET) provided Measured Intensity vs. Time Data Set. (Note that "ANL", the Rotating Analyzer Azmuthal Angle in EQ. 1 which is the argument of the COS and SIN Trig Functions, is a function of time). Multiple D.C. measurements can also form a Data Set which can be utilized in determination of ellipsometric ALPHA and ellipsometric BETA, (eg. a select set ellipsometric ALPHA and ellipsometric BETA Values corresponding to a number of Azimuthal angular settings of "ANL").

Ellipsometric ALPHA and ellipsometric BETA are generally, but not necessarily, found by a "Fourier Analysis" approach as applied to an appropriate Data Set obtained at a Detector System (DET) in an Ellipsometer System. Some procedures then apply mathematical corrections to the so-determined ellipsometric ALPHA and ellipsometric BETA parameters to provide ellipsometric ALPHA PRIME and ellipsometric BETA PRIME parameters in an attempt to minimize the effects of Polarization Dependence Sensitivity, electrical signal gain in amplifiers and the like. Other mathematical manipulations can also be performed, such as signal compensating for wavelength dependent attenuation etc.

However, whether mathematical manipulation of the measured ellipsometric ALPHA and ellipsometric BETA is done or not, the purpose of determining the ellipsometric ALPHA and ellipsometric BETA parameters in Rotating Element Ellipsometers (REE's) is generally to allow the mathematical calculation of well known Sample System (SS) Characterizing Ellipsometer PSI and DELTA Constant parameters by means of, for instance, Transfer Functions. Said PSI and DELTA Constant parameter values being representative of an investigated Sample System (SS) optical properties, (eg. such as refractive index, extinction coefficient and even temperature), and for instance, of the thickness and composition of a thin film(s) present on the surface of a Sample System. The conversion of measured ellipsometric ALPHA and ellipsometric BETA parameters to calculated PSI and DELTA values can be by means of well known Transform Equations. See Eqs. 2 and 3 for the general form of equations which apply to Rotating Analyzer Ellipsometer (RAE) systems, in the case wherein an isotropic Sample System is being investigated:

$$TAN(PSI) = \frac{\sqrt{1+ALPHA} \; ABS(TAN(POL))}{\sqrt{1-ALPHA}} \quad \text{EQ. 2}$$

$$PSI = ARCTAN\left(\frac{\sqrt{1+ALPHA} \; ABS(TAN(POL))}{\sqrt{1-ALPHA}}\right)$$

$$COS(DELTA) = \frac{BETA}{\sqrt{1-ALPHA^2}} \quad \text{EQ. 3}$$

$$DELTA = ARCCOS\left(\frac{BETA}{\sqrt{1-ALPHA^2}}\right)$$

where (POL) is an angle set by a Polarization State Generator, (see description of a Rotating Analyzer Ellipsometer System infra), which is easily controlled by a user. As the angle (POL) is changed, it will be observed from Eq. 2 that the measured value of ellipsometric ALPHA involved in arriving at a Sample System Constant PSI value will change. For other (REE's) similar equations exist. For example in (RPE) systems, the angle (POL) in Eqs. 2 and 3 is replaced by an angle (ANL), the Azimuthal angle of an Analyzer, with similar modification being made in Equation 1. It is noted that modified equations apply where anisotropic or anisotropic-depolarizing Sample Systems are investigated, but similar benefits to those exemplified by EQS. 2 and 3, which are valid for the case where an isotropic Sample System is investigated, result from practice of the present invention where anisotropic or anisotropic-depolarizing Sample Systems are investigated.

(Note, Equations 1 and 2 are derived in standard texts on Ellipsometer, such as "ELLIPSOMETRY AND POLARIZED LIGHT" by Azzam and Bashara, North Holland, 1977, and discussed in a Review Article by Collins, title "AUTOMATIC ROTATING ELEMENT ELLIPSOMETERS: CALIBRATION, OPERATION, AND REAL-TIME APPLICATIONS:, REV. SCI. INSTRUM. 61 (8) AUGUST 1990. These references are incorporated by reference into this Disclosure.)

Observation of Eq. 2 shows that an ellipsometric ALPHA value of approximately one (1.0) will cause the equation denominator to go to zero (0.0), and the value provided by said equation for any set Polarization State Generator Polarizer, Polarizer (P) set Angle (POL), to be infinity. Such a result defeats the goal of Ellipsometric Analysis. If, however, ellipsometric ALPHA is approximately zero (0.0) then Eq. 2 will be sensitive to changes in the Polarization State Generator (PSG), Polarizer (P) set Angle (POL), and not ellipsometric ALPHA. This is a desirable situation as noise and errors in measurement etc. of ellipsometric ALPHA value are eliminated while the Polarization State Generator (PSG), Polarizer (P) set Angle (POL) remains controllable by a user. Now, it is known that different settings of the Polarization State Generator (PSG), Polarizer (P) set Angle (POL), are associated with different values of ellipsometric ALPHA. That is, a user controlling the Polarization State Generator (PSG), Polarizer (P) set Angle (POL) can effect a desired Detector System (DET) measured value of ellipsometric ALPHA. As indicated, ideally one would want ellipsometric ALPHA t be zero (0.0), however, it will be noted that any ellipsometric ALPHA value below about nine-tenths (0.9) will serve to greatly reduce the effect of noise and errors in measurement etc. in ellipsometric ALPHA, in the calculation of PSI via Eq. 2. That is, while preferable, it is not absolutely required that the value of ellipsometric ALPHA be zero (0.0) to sufficiently decrease the sensitivity of Eq. 2 to changes in ellipsometric ALPHA such as can occur because of noise, or because of errors in measurement or determining ellipsometric ALPHA by evaluating to EQ. 1 in view of a measured Detector provided Data Set, for instance. (That is, Data can be obtained which can be utilized in Calculating PSI and DELTA Values when ellipsometric ALPHA is not zero (0.0), even though that is an Optimum Value for ellipsometric ALPHA).

As was alluded to infra, it is well known, in (RAE) systems, to adjust the Polarization State Generator Angle (POL) to set a desired ellipsometric ALPHA value in practice. What has not been possible, prior to the present invention, however, is the ability to conveniently, (and simultaneously), provide control of ellipsometric BETA values, over a relatively large range of wavelengths, (eg. one-hundred-ninety (190) to seventeen-hundred (1700) nanometers), for a similar reason as described with respect to ellipsometric ALPHA. (Note that similar procedures are applicable in other (REE's)). Inspection of Eq. 3 shows that calculation of DELTA, (again a Sample System (SS) characterizing parameter which is constant for a given (AOI) and Wavelength), requires knowing a measured parameter ellipsometric BETA. It occurs, in certain ranges of ellipsometric BETA parameter values, that ellipsometric BETA is very sensitive to unavoidable noise and measurement errors etc. introduced in conducting an investigation of a Sample System (SS). Hence, just as is the case with ellipsometric ALPHA, it would be desirable to be able to control the value of ellipsometric BETA so that it is in a range where the effect of noise and errors in measurement etc. ellipsometric BETA, in the Eq. 3 transfer function which provides DELTA, are negligible. As with ellipsometric ALPHA, a value of zero (0.0) is ideal, but not absolutely required.

To date no known system and method has been available to allow convenient ellipsometric BETA Value range control capability over a relatively large spectroscopic range of wavelengths, without contributing undesirable artifact content which can be prohibitively difficult to compensate out, emphasis added.

There is thus demonstrated a need for a system and method that will allow a user to adjust an Ellipsometer System during use, such that both measured ellipsometric ALPHA and ellipsometric BETA parameter values can be simultaneously set to values in ranges wherein noise and errors in measurement thereof etc. have negligible effect on the calculation of PSI and DELTA by Transfer Function Eqs. 2 and 3. As noted with respect to Eq. 1 infra, numerous pairs of ellipsometric ALPHA-ellipsometric BETA values can satisfy EQ. 1. Some values of ellipsometric ALPHA, (ie. near zero (0.0) or at least less than nine-tenths (0.9)), however, will be found to decrease the sensitivity of Eq. 2 to noise and measurement errors etc. in ellipsometric ALPHA as compare to that present when greater Values of ellipsometric ALPHA are utilized. As well, some relatively low values of ellipsometric BETA will decrease the sensitivity of Eq. 3 to noise and measurement errors in ellipsometric BETA. If a user could then adjust an Ellipsometer System so that Eqs. 2 and 3 are provided ellipsometric ALPHA and ellipsometric BETA Values nearer zero (0.0) than to one (1.0), said ellipsometric ALPHA and ellipsometric BETA Values being arrived at by, for instance Fourier Analysis, in view of a set of Data obtained experimentally from said Detector System (DET), then said Ellipsometer System provided data would be made insensitive to noise and errors in measurement etc. in arriving at ellipsometric ALPHA and ellipsometric BETA values, as said noise and errors in measurement effect calculation of PSI and DELTA values from Eqs. 2 and 3. The present invention provides a system and method for allowing control over the measured ellipsometric BETA value, in addition to the measured value of ellipsometric ALPHA.

Figure 2:
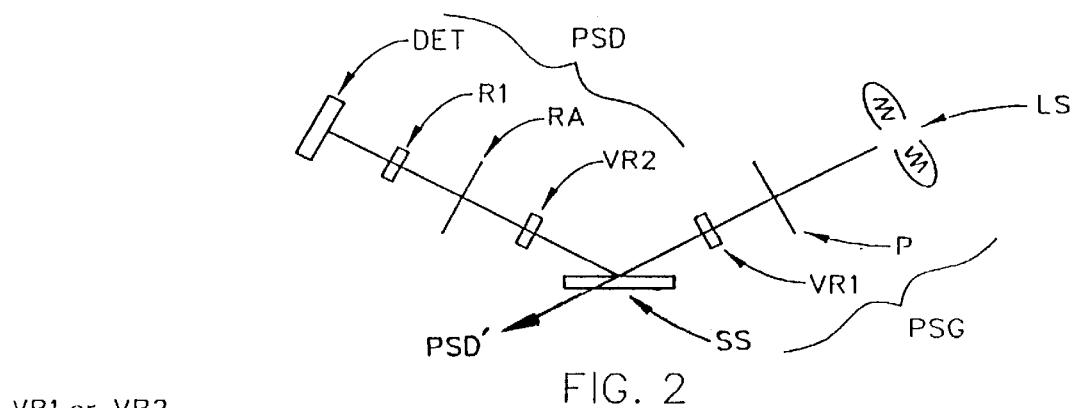
FIG. 2 shows the typical Variable Angle Spectroscopic Ellipsometer (VASE) System of FIG. 1 with Variable Retarders added between the Polarizer and Rotating Analyzer.

The present invention can be most easily understood by reference to FIGS. 1 and 2. As mentioned infra, FIG. 1 shows a typical J.A. Woollam Co. Variable Angle Spectroscopic Rotating Analyzer (RAE) Ellipsometer, (VASE) System which is being used as an example Ellipsometer system herein. Shown are a Light Source (LS) which provides a beam of light, a Polarizer (P), a Sample System (SS), a Rotating Analyzer (RA) a Retarder (R1) and a Detector System (DET). FIG. 2 shows the system of FIG. 1 with added Variable Tilt Retarders (VR1) and (VR2). As described above, said Retarder (R1) can be positioned after the Rotating Analyzer (RA) and ahead of the Detector System (DET) and serves to reduce the effect of Polarization Dependence Sensitivity of a Detector System (DET) in use. However, Variable Retarders (VR1) and (VR2) are placed ahead of the Rotating Analyzer (RA). (Note, (VR1) is present in the Polarization State Generator System (PSG), and (VR2) is present in the Polarization State Detector Reflectance (PSD) or Transmission (PSD') System. One or both (VR1) and (VR2) can be present, or only one thereof might be present. The point is that the presence of a Variable Retarder at the location of (VR1) and/or (VR2) allows a user an adjustment by which the measured ellipsometric BETA parameter value can be set. While it is not unknown to place Variable Retarders in Ellipsometer Systems such as shown in FIG. 2, the use made thereof disclosed herein is, within the knowledge of the Inventors, new. Known uses of Variable Retarders placed as are (VR1) and (VR2) are, for instance, to effect circular polarization on a Polarized Beam of Light in the vicinity of the Sample System, (so that, for instance, Mueller Matrix components can be measured, see Azzam and Bashara reference cited infra). In the present scenario, however, such is not the primary purpose and it will be appreciated that once the Polarized Beam of Light passes through the sequentially following Rotating Analyzer (RA), it will again be Linearly Polarized. Also, it must be understood that the present invention Variable Retarder(s) can be present in addition to other Variable Retarders which are present specifically to allow determination of Mueller Matrix components.

Continuing, reference to Eq. 4 shows the effect of (VR1) and/or (VR2).

$$COS(DELTA + R) = \frac{BETA}{\sqrt{1 - ALPHA^2}} \qquad EQ. 4$$

$$DELTA = ARCCOS\left(\frac{BETA}{\sqrt{1 - ALPHA^2}}\right) - R$$

where the "subtracted-out" "R" value is the amount of Retardation provided by (VR1) and/or (VR2) which contributed to the value of BETA which was measured. (Note, EQ 4 is technically valid only where the fast axis of the Variable Retarder is in the "P" or "S" plane, however, said equation generally demonstrates the effect utilized by the present invention).

Comparison to Eq. 3 shows that the argument of the COS term has been modified by the addition of the Retardation effected by the presence of (VR1) and/or (VR2). Alternatively, it can be stated that an "Offset" is added to the Equation for calculating DELTA by the "Tilt" of (VR1) and/or (VR2), thereby effecting a change of the value of the measured ellipsometric BETA parameter. Again, said measured value can be set to be, ideally, near zero (0.0), although any reduction in a measured value thereof is beneficial.

In use a routine which allows measuring an ellipsometric ALPHA and ellipsometric BETA pair solution to EQ. 1, (typically as arrived at by Fourier Analysis of a Data Set provided experimentally at the Detector System (DET)), will be followed. Said routine provides an ellipsometric ALPHA value in a range which is not significantly sensitive to noise and errors in measurement etc. involved in arriving thereat, so that in application of Eqs. 2, (which it will be recalled allows calculation of PSI from a measured ellipsometric ALPHA value), the effect of noise and errors in measurement and etc. of ellipsometric ALPHA are negligible. As well, said routine allows setting a measured ellipsometric BETA Value in a range in which it is not significantly sensitive to noise and errors in measurement etc. thereof.

Figure 3A:
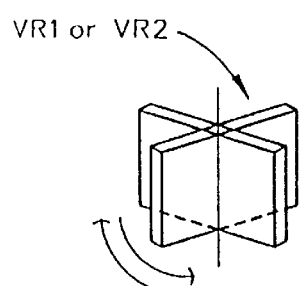
FIGS. 3a and 3b. show Azimuthal and Elevational "Tilts" respectively which can be applied to Berek-type Variable Retarders, when such comprise the Variable Retarders shown in FIG. 2.
Figure 3B:
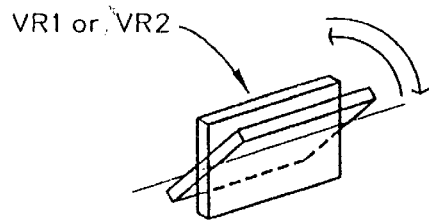

Now, it will be appreciated that Retarders (VR1) & (VR2) can each physically constitute a Plate of a finite thickness, presenting with offset essentially parallel surfaces. (Note, however, that no Retarder is physically perfect). Such a Plate can be "Tilted" in many ways. Two preferred axes of rotation are demonstrated in FIGS. 3a and 3b. FIG. 3a shows Azimuthal Tilt around a Vertical Axis and FIG. 3b shows Elevational Tipping around a Horizontal Axis. Note that both Clockwise and Counterclockwise Rotations can be effected in both the Azimuthal and Elevational cases. Such multidirectional Tilt adjustment capability allows adjusting-out the effect of imperfections, which vary from Retarder to Retarder, in the context of an Ellipsometer System. (For instance, one imperfection which occurs is that the optical Axis of a Retarder is oriented other than exactly perpendicular or parallel to the surface of the Retarder. The ability to effect multidirectional "tilting" of such a Retarder allows matching the (AOI) of an impinging Beam of Light essentially "exactly" as desired with respect to the actual direction of the Polarization Axis of a Retarder. This capability, as far as the Inventors know, has not previously been available in an Ellipsometer System).

It is also noted that a preferred Retarder, the general nature of which was described directly infra, is a Berek-Type Magnesium Fluoride Plate with a bandwidth of operation in excess of the one-hundred-ninety (190) to seventeen-hundred (1700) nanometers. Utilized in the Rotating Analyzer Ellipsometer System being described, (eg. a VASE System), which Berek-Type Magnesium Fluoride Plate provides an effective Retardance, variable over a range of from zero (0.0) to in excess of plus or minus ninety (90) degrees, over said entire range of frequencies for one-hundred-ninety (190) to seventeen-hundred (1700) nanometers. (Note that Saphire might also a usable material from which a Berek-Type Retarder can be made as is Mica. Mica, however, becomes opaque in certain wavelength regions of interest. As well, Quartz, even though being Optically active in that it rotates a Polarized Beam of Light, is also a possible material for a Berek-type Retarder). It is noted that preferred Berek-Type Magnesium Fluoride Plates are available from New Focus, Inc., and are identified as a (Berek Polarization Compensator 5540).

FIG. 4a shows a Beam of Light incident upon a Berek-type Retarder Plate at a an Angle of Incidence (AOI) of zero (0.0) degrees thereto, (ie. the angle between the normal to the surface of the Retarder Plate and the impinging Beam of Light is zero (0.0) degrees). In an ideal Berek-Type Retarder the Optical axis is perpendicular to the plane of the surface (s) of the Retarder plate, and the Polarization State of a Polarized Beam of Light which is aligned with the Optical Axis so as to impinge at said ninety (90) degree angle to said surface(s), is not significantly affected as it passes therethrough. In practice, the Optical Axis of a Berek-Type Retarder can be slightly off perpendicular to the surface of thereof, and the surfaces thereof may not be exactly parallel to one another, but a multiaxis tilting procedure can be utilized to effect coincidence between the direction of the Polarized Beam of Light and the actual effective Optical Axis. Said multiaxis tilting procedure will generally be found to be require different amounts of tilt for each specific Berek-Type Retarder because of manufacturing variance from one unit to another.

It is noted that Retarders with an Optical Axis parallel to the surface thereof, (zero, or multiple-order-waveplates), could possibly be used in the present invention, instead of Berek-type Retarders, but a problem with doing so with presently commercially available systems exists as such systems do not simply apply a direct amount of retardation to a Polarized Beam of Light to effect, for instance, a variable zero (0.0) to ninety (90) degree retardation. Rather, two plates are typically involved in commercially available zero, and multiple-order-waveplate Retarder Systems which have the Optical Axis parallel to the surface. Said systems are designed such that one plate, for instance, effects a five-thousand (5000) degree retardation in one direction of rotation, and a second plate provides a fourth-thousand-nine-hundred-ten degree (4910) retardance in the opposite direction of rotation. The end effect on a Polarized Beam of Light exiting the described System then is an introduced of retardation to a Primary Polarized beam of an intended ninety (90) degrees. In addition, it has been found that presently Commercially available Retarders with the Optical Axis in the plane of the Surface thereof, (eg. zero, and multiple-order-waveplates), are used, multiple such systems in sequence are required to effect a Variable Retardance over the entire range of zero (0) to ninety (90) degrees, over a relatively large spectroscopic range of wavelengths, (eg. one-hundred-ninety (190) to seventeen-hundred (1700) nanometers and greater). This results because over a relatively large spectroscopic range of wavelengths, which range includes therein wavelengths which are half as long as others in said relatively large spectroscopic range, a zero, or multiple-order-waveplate Retarder will serve only to provide one-hundred-eighty (180) degrees of retardation at said half wavelength lengths. That is it will simply rotate the orientation of a linearly polarized wave rather than provide it with any elliptical influence. (It is noted that to provide a full zero (0.0) to ninety (90) degrees of Retardation at all wavelengths in the identified spectroscopic range of wavelengths, requires three (3) fixed zero-order-waveplate Retarders in series to avoid the identified one-hundred-eighty (180) degree "rotated orientation" sign problem).

It is noted that any system which allows sufficient user control of Retardance over the identified relatively large spectroscopic range of wavelengths can be used in the present invention. Numerous possible types of Variable Retarders were identified herein infra. However, for the present, Berek-Type Retarders are preferred as problems, (such as contribution of artifact content to a polarized beam of light passed therethrough), in the use thereof have been found to be minimal, as compared to problems encountered when, for instance, multiple presently commercially available zero, and multiple-order-waveplates are utilized.

It is also noted that the presence of a Variable Retarder (VR1) and/or (VR2) as shown in FIG. 2 allows determination of the direction of rotation, (the "Handedness") of a polarized Beam of Light. Introduction of a Retardation "R" will effect the Polarization State by adding to, or subtracting from an existing Polarization State, depending on the "Handedness" thereof. By detecting the direction of the effect of adding Retardance "R", one knows the "Handedness" of the Polarized Beam of Light acted upon. "Handedness", it is noted, is otherwise not determined by an Ellipsometer System. Prior to the present invention "Handedness" has been determinable in an ellipsometer which has been effectively converted to a polarimeter by obtaining a set of ALPHA and BETA values, entering a ninety (90) degree Retarder into the ellipsometer/polarimeter system, and obtaining a second set of ALPHA and BETA values. The present invention allows utilizing other than ninety (90) degrees retardance when obtaining the second set of ALPHA and BETA values. "Handedness" is described in a paper by Hauge and Dill titled "Design and operation of ETA, an Automated Ellipsometer", IBM J. of Dev. and Research, Vol. 17, No. 6, November 1973, which reference is incorporated by reference in this Disclosure. As well, the presence of Retarders in the position of (VR1) and (VR2), in combination with a Rotating Analyzer in an Ellipsometer System allows determination of elements of a Mueller Matix if said Retarder is caused to "Tilt—for Berek-type Retarder" or "Rotate—for other type Retarder". This is yet another benefit of the presence of a Retarder (VR1) and/or (VR2) as shown in FIG. 2. (Note, VR2 must be present to completely determine Fifteen elements of a Normalized Meuller Matrix). With the presence of Retarders (VR1) and (VR2) in the positions shown, if both are "tilted" or rotated during use while the Analyzer (RA) and Polarization State Generator (PSG) are held stationary, determination of Fifteen (15) elements of a Normalized Mueller Matrix is possible. The meanings of the term "Mueller Matrix" is well known in the field of Ellipsometry and Polarimetry and will not be further discussed here. An article titled "Recent Developments In Instrumentation In Ellipsometry", by Hauge, Surface Science, Vol. 96, No. 108, 1980 describes Stoles Vectors and Mueller Matrices and said reference is incorporated by reference in this Disclosure.

Figure 4D:
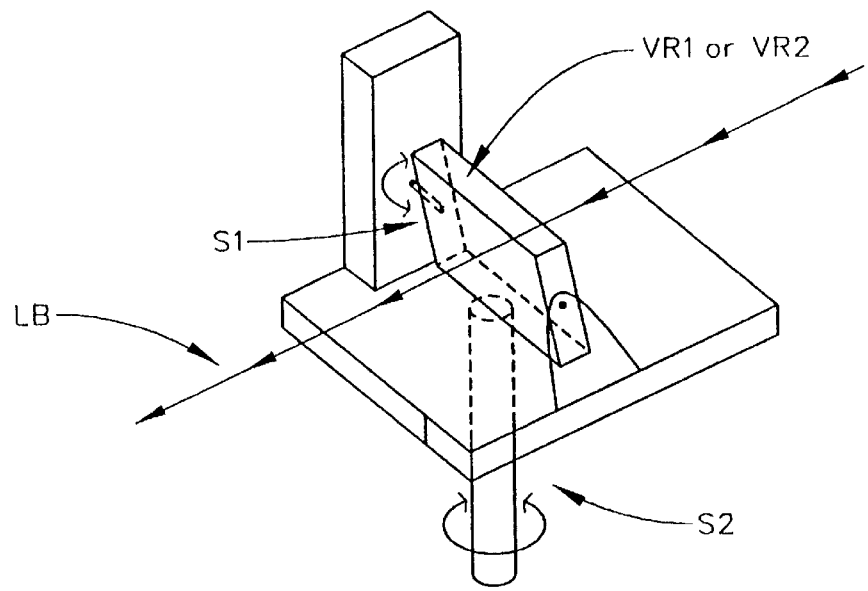
FIGS. 4d and 4e show multi-tilt Berek-type Variable Retarder systems.
Figure 4E:
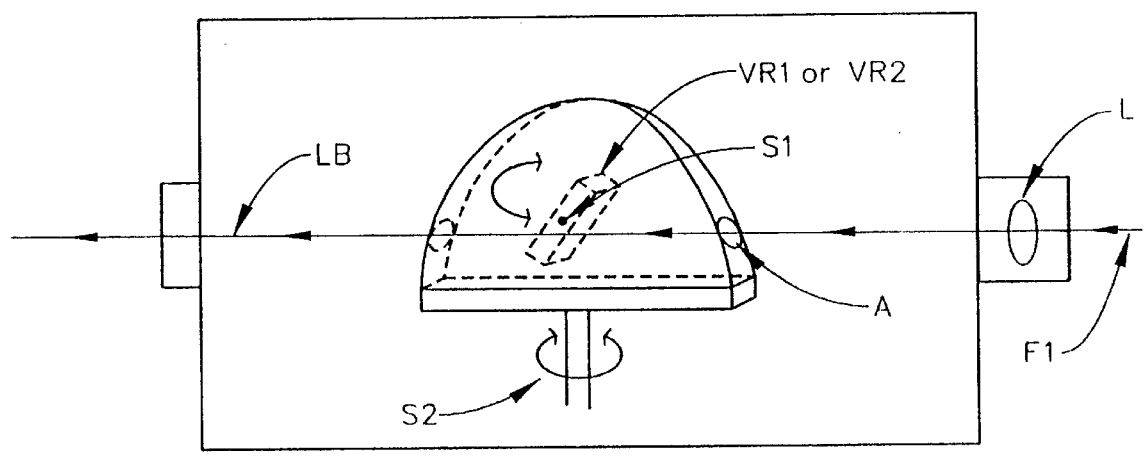

Various modes of operation of Ellipsometer systems as shown in FIGS. 1 and 2, without, and fitted with the present ellipsometric BETA control Retarder(s) (VR1) and/or (VR2), respectively, present in view of FIGS. 3a, 3b and 4a–4e. FIGS. 4a–4c were discussed infra. FIGS. 3a and 3b show two axes of "Tilt" of a Berek-type Variable Retarder (VR) such as utilized in the exemplary J.A. Woollam CO. Inc. VASE Rotating Analyzer Ellipsometer (RAE) System utilized in this Disclosure to obtain the results demonstrated in FIGS. 5a–5d, 6, and 7a–7f, discussed supra. FIGS. 4d and 4e show Rotation of said Berek-type Variable Retarder (VR) around mutually perpendicular shafts (S1) and (S2). Shown also is a Light Beam (LB) passing through said Berek-type Variable Retarder (VR) FIGS. 4d and 4e. FIG. 4e provides another view of a two axes of "tilt" Berek-type Variable Retarder (VR) with a Light Beam (LB) passing therethrough. FIG. 4e also shows a Fiber (F1) carrying said Light Beam (LB) to Focusing Lens (L). Said Light Beam (LB) is shown passing through a Berek-type Variable Retarder (VR) via an aperture (A) in a housing therefore.

A Case 1 No-Plate Mode refers to a scenario in which neither Variable retarder (VR1) or (VR2) is present, and in which the Polarizer (P) is adjusted to set ellipsometric ALPHA in an insensitive range and a resulting ellipsometric ALPHA-ellipsometric BETA pair is directly provided from the Detector System (DET) Data, typically by a Fourier Analysis procedure applied to modulated intensity data in (REE's).

A Case 2 No-Plate Regression Mode refers to a scenario in which neither Variable Retarder (VR1) or (VR2) is present, and in which a number of Polarizer (P) settings are effected and a Data Set comprised of a number of ellipsometric ALPHA-ellipsometric BETA pairs, provided by analysis of data provided by the Detector System (DET), are mathematically subjected to a regression procedure to determine "most likely" PSI and DELTA Values in view thereof. This approach to PSI and DELTA evaluation does not impose any control on the value of ellipsometric BETA, however, this approach to determining PSI and DELTA is itself considered by the Inventors to be new, novel, nonobvious and useful.

A Case 3, Plate-Zero-Mode is identified wherein an ideal Berek-Type Variable Retarder (VR1) and/or (VR2) is/are present, as shown in FIG. 2. Said Berek-type Variable Retarder(s) has/have the optical Axis thereof oriented perpendicular to the surface thereof. If the beam of light is incident along the Optical Axis of said Berek-type Variable Retarder Plate, as shown in FIG. 4a, then except for minor attenuation, the Variable Retarder Plate has no effect. Thus an Ellipsometer system can include such a Berek-Type Variable Retarder Plate which need not be physically removed when not used in certain instances. Simple alignment will make its presence essentially undetectable, thereby making use of the Ellipsometer System much more convenient. (Note, multiple axis "Tilt" capability allows orienting the Berek-type Variable Retarder so that its presence is end-user Transparent at any wavelength over the large range of at least one-hundred-ninety (190) to seventeen-hundred (1700) nanometers). This convenience, to the inventor's knowledge, has not here-to-fore been available in any ellipsometer system.

Two Cases, in addition to the above mentioned Case 3 Plate-Zero-Mode, apply to an Ellipsometer System in which Variable Retarder(s) (VR1) and/or (VR2) is/are present.

The Inventors define a significant Case 4 VASE-C MODE.

Figure 5A:
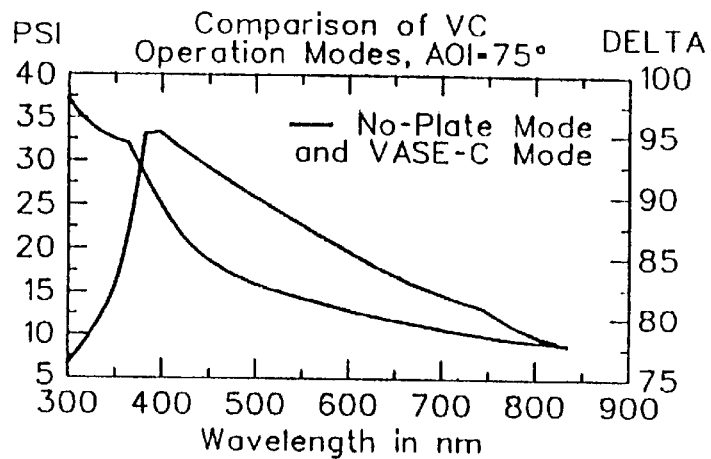
FIGS. 5a through 5d show plots of Sample System characterizing PSI and DELTA values as a function of wavelength of light utilized in a beam of polarized light, applied to a Sample System at seventy-five (75) and at thirty (30) degrees Angles of Incidence, as arrived at by various Modes of operation.
Figure 5B:
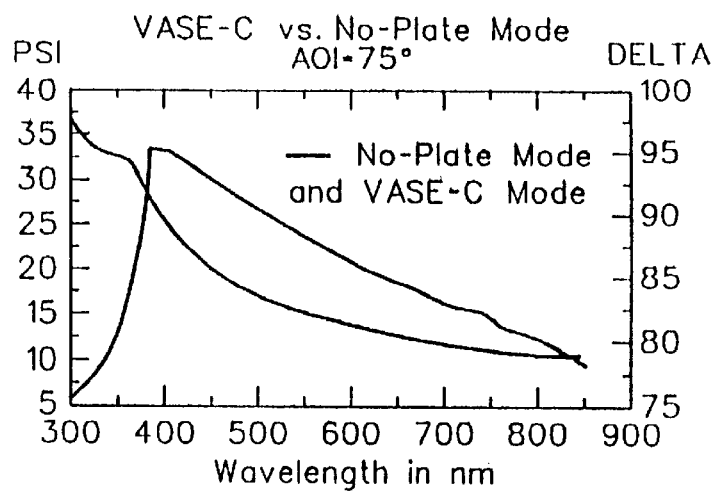
Figure 5C:
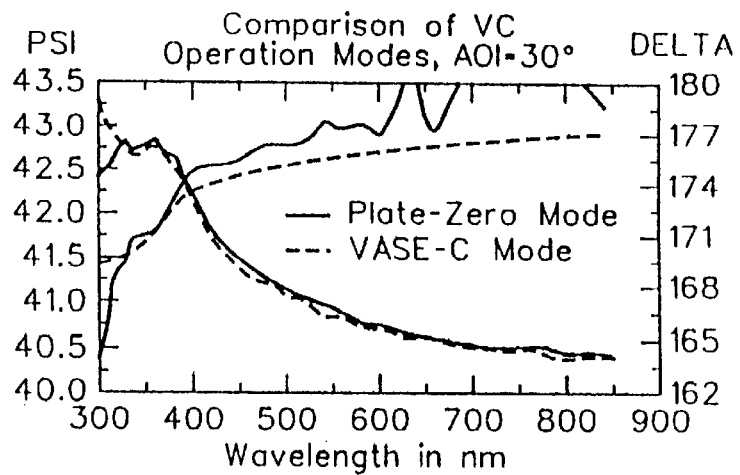
Figure 5D:
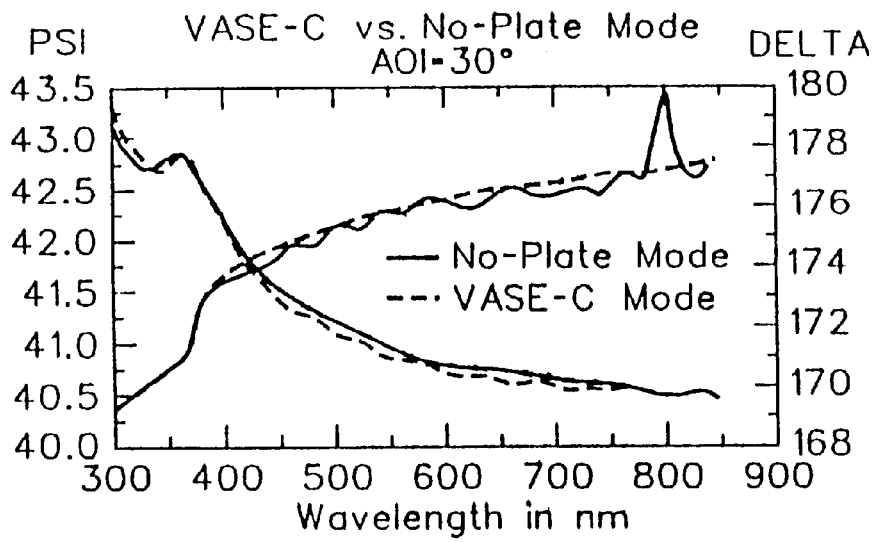
Figure 6:
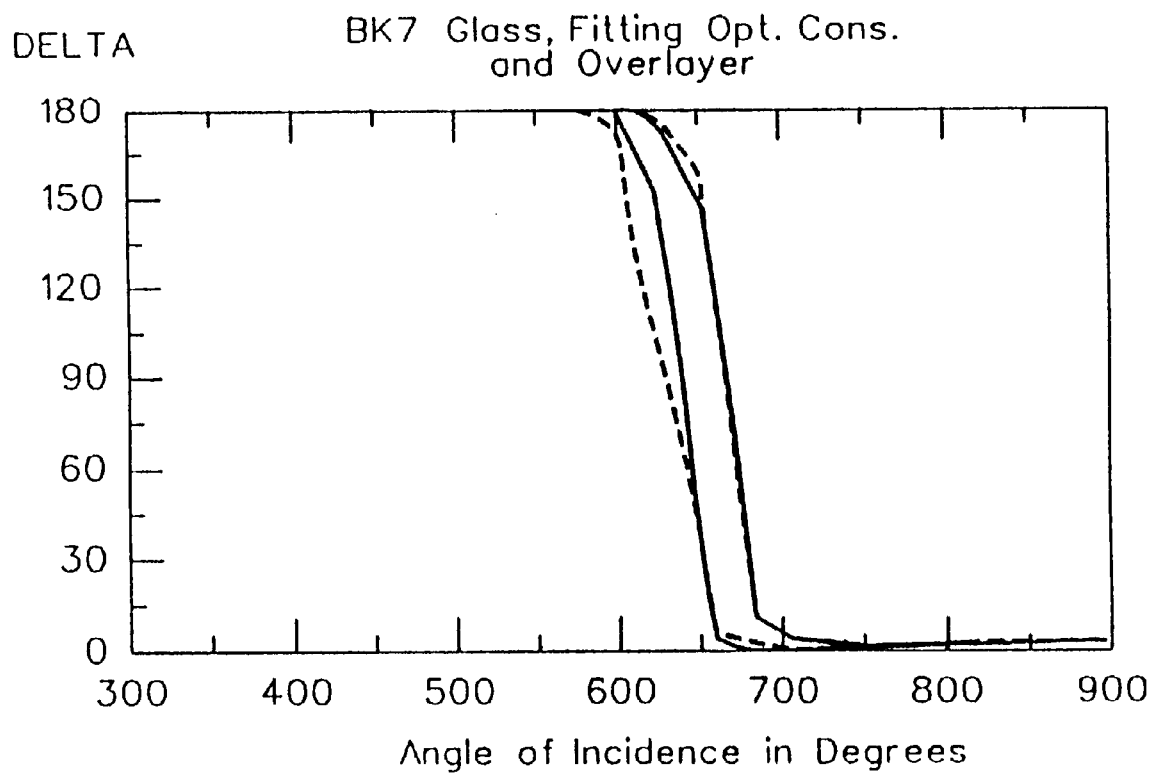
FIG. 6 shows DELTA values as a function of the Angle of Incidence of a beam of polarized light to a Thick Glass Sample System, said DELTA values being determined by a present invention operation Mode method.

FIGS. 5 through 7, (discussed supra), show results obtained using this Mode of operation. In the specific tests demonstrated in said Figures, two (2) (RAE) Polarizer Angle (POL) positions were used, and Five (5) Variable Retarder positions were used at each thereof, leading to a collection of Ten (10) data ellipsometric ALPHA-ellipsometric BETA pair values. The Five Variable Retarder Positions correspond to Zero (0.0) Tilt, a Clockwise and a Counter-Clockwise Azimuthal Tilt and a Clockwise and a Counterclockwise Elevational Tilt, (see discussion with respect to FIGS. 3a and 3b infra). (Note that forty-five (45) degree Tilts were utilized to acquire the data which was utilized to calculate the PSI and DELTA values plotted in FIGS. 5–7). A Mathematical Regression was applied to said ten (10) ellipsometric ALPHA-ellipsometric BETA pair data to find Constant PSI and DELTA parameters which provide the best fit by a minimized Square Error approach. (Said Regression Procedures are well known to those knowledgeable in the field of Ellipsometry and other areas in which data fitting to mathematical models is utilized. The most commonly used version goes by the name "Marquardt-Levenberg" and involves standard non-linear techniques of equation parameter evaluation). It is to be noted that in this case some of the ten (10) ellipsometric ALPHA-ellipsometric BETA pairs will not have ellipsometric ALPHA and/or ellipsometric BETA values which are in ranges which are insensitive to noise and errors in measurement etc., but application of the Mathematical Regression approach to evaluating PSI and DELTA in view of the plurality of ellipsometric ALPHA-ellipsometric BETA pair data, provides a result which is surprisingly good, emphasis added. The regression technique reduces the importance of less than optimum ellipsometric ALPHA-BETA pairs for two reasons. First, the less optimum ellipsometric ALPHA-BETA pairs tend to have large uncertianties, (are noisier), and the regression is made to weight the ellipsometric ALPHA-BETA pair inversley with respect to noise. Second, the "Effective Transfer Function" associated with the regression automatically applies information contained in the fitting model which limits the influence of less optimum ellipsometric ALPHA-BETA pairs. That is, ellipsometric ALPHA-BETA pairs obtained utilizing an (AOI) near to a Brewster Angle have maximum sensitivity, (eg. less associated error in measurement is possible), to physical properties of a Sample System. (Note, it is to be understood that the use of Ten (10) ellipsometric ALPHA-ellipsometric BETA pairs was arbitrary and that other numbers of ellipsometric ALPHA-ellipsometric BETA pairs could be used by changing the number of (AOI's) and number of Retarder "Tilt" positions so as to arrive at other than ten ellipsometric ALPHA-ellipsometric BETA parameter values for use in the Regression evaluation of PSI and DELTA). It is noted that the only difference between Case 2 and Case 4 is that in Case 4, a ellipsometric BETA affecting Retarder Plate present in the Ellipsometer System and is utilized as a means to control measured ellipsometric BETA values while collecting ellipsometric ALPHA-ellipsometric BETA pair data. That is Case 2 also utilizes a Mathematical Regression approach to arriving at PSI and DELTA.

A Case 5 Plate-Mode refers to a scenario in which ellipsometric ALPHA is set to a value in a range where it is insensitive to noise and measurement errors etc. by adjustment of the Polarizer, and ellipsometric BETA is set to a value in a range where it is similarly insensitive by adjustment of Variable Retarder(s) (VR1) and/or (VR2). Then as in Case 1, Fourier Analysis, (or some similar technique), is applied to data acquired from the Detector System (DET) to evaluate an ellipsometric ALPHA and an ellipsometric BETA. The only difference between Case 1 and Case 5 is that in Case 5 an ellipsometric BETA affecting Retarder Plate is present in the Ellipsometer System and utilized to set ellipsometric BETA to an insensitive region value in use.

FIGS. 5a and 5b demonstrate PSI and DELTA plots achieved from data acquired where an (AOI) of seventy-five (75) degrees was utilized. FIG. 5a shows a comparison between Case 3 Plate-Zero Mode and Case 4 VASE-C data and FIG. 5b shows a comparison between Case 1 No-Plate Mode and Vase-C mode. Note that at a seventy-five (75) degree (AOI) all modes provide good PSI and DELTA data. FIGS. 5c and 5d show plots achieved from data acquired similarly to how data was acquired for the plots in FIGS. 5a and 5b respectively, but where an (AOI) of thirty (30) degrees. Note that only the Case 4 VASE-C mode provides good DELTA data.

FIG. 6 shows DELTA calculated from data achieved from data acquired by investigating Thick BK7 Glass using a Case 4 VASE-C Mode where the (AOI) was varied from fifty (50) to sixty-two (62) degrees. Note that reliable DELTA values are achieved near zero (0.0) and one-hundred-eighty (180) degrees, where reliable values for DELTA are not ordinarily obtainable. (It will be recalled that an (AOI) near the Principal or Brewster Angle must typically be utilized to allow obtaining reliable values for DELTA, and said reliable values are then near ninety (90) degrees).

Figure 7A:
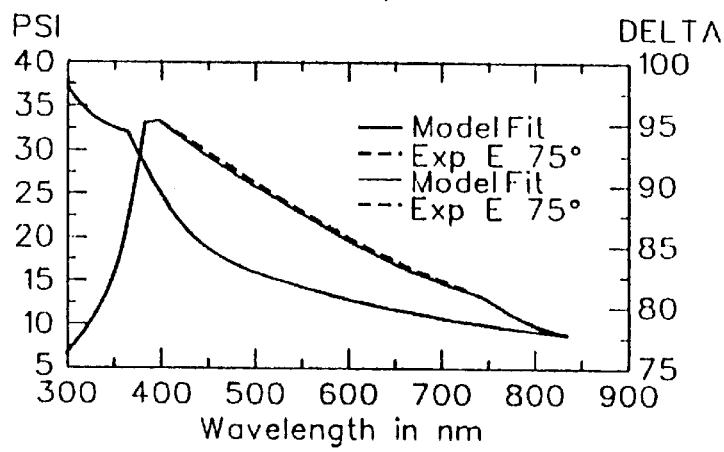
FIGS. 7a through 7f show plots of Sample System characterizing PSI and DELTA values as a function of wavelength of light utilized in a beam of polarized light, applied to a Sample System at seventy-five (75) and at thirty (30) degrees Angles of Incidence, as arrived at by various Modes of operation of the ellipsometer.
Figure 7B:
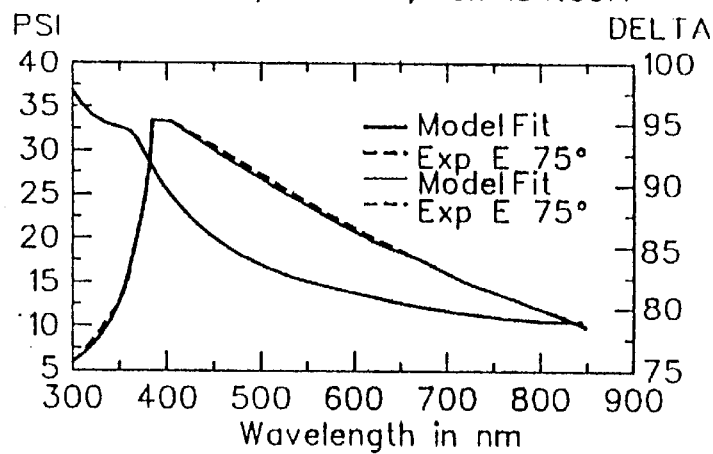
Figure 7C:
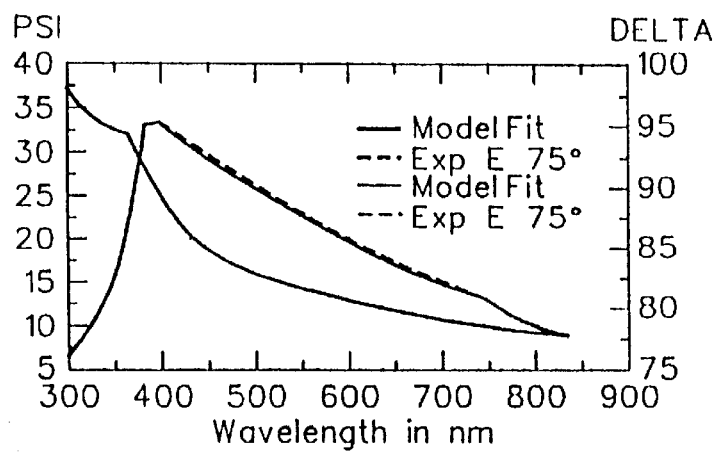
Figure 7D:
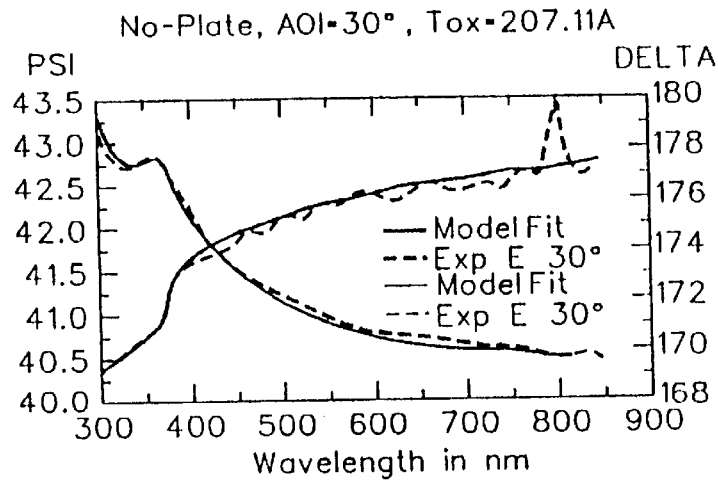
Figure 7E:
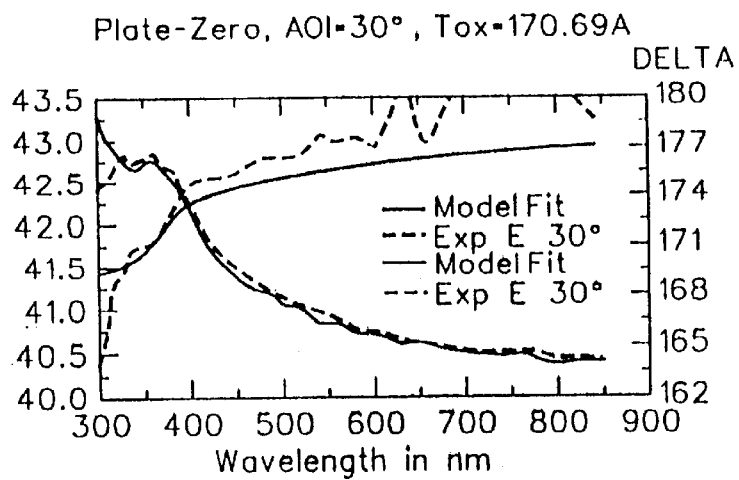
Figure 7F:
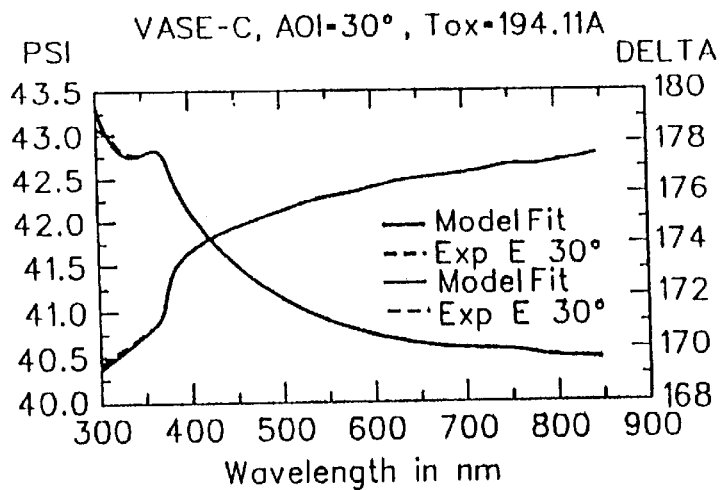

FIGS. 7a–7f show additional PSI and DELTA plots achieved from data acquired from various of the Modes identified above. FIGS. 7a–7c are for data acquired using an (AOI) of seventy-five (75) degrees, and FIGS. 7c–7f are plots achieved from data acquired using an (AOI) of thirty (30)) degrees. FIG. 7a is for a Case 1 No-Plate Mode, FIG. 7b is for a Case 3 Plate-Zero Mode and FIG. 7c is for a Case 4 VASE-C Mode. Note that the PSI and DELTA values shown in FIGS. 7a–7c are all good. Note however, that the DELTA values shown in FIG. 7f is superior to that shown in FIGS. 7d and 7e. That is, where the (AOI) is set at thirty (30) degrees, only the Case 4 VASE-C approach to calculating DELTA provided a very good result over the full spectrum of wavelengths shown.

In view of the foregoing, it is to be understood that the most important results shown by said Inventors provided Test Results are:

1. Use of the Case 4 VC VASE-C Mode in evaluating PSI and DELTA parameters allows greatly reduced restraints on the Angle of Incidence (AOI) of a Sample System Probing Polarized Beam of Light, (said (AOI) being with reference to the surface of a Sample System being investigated). That is, for instance, PSI and DELTA Values for a Semiconductor can be found by Regression on data obtained with the (AOI) at seventy-five (75) degrees, which is the Principal or Brewster Angle as is well known. With the present invention in place, however, the quality of data obtained with the (AOI) set to thirty (30) degrees, for instance, allows PSI and DELTA Value determination equally as well when a Case 4 VASE-C Mode approach is utilized. Again, this means that the (AOI) need not be set to the Principal or Brewster Angle to obtain high quality Data. Those knowledgeable in the field of Ellipsometry will immediately recognize the surprising nature of this result. (Note that the PSI and DELTA Values obtained at different (AOI's) are not the same Values, but that the Data obtained with the (AOI) set to thirty (30) degrees is of a quality associated with data taken at the Principal or Brewster Angle. Again, where a Semiconductor is the Sample System, the (AOI) is typically set at the Brewster Angle of approximately seventy-five (75) degrees, where DELTA is near ninety (90) degrees, and ellipsometric BETA becomes a minimum, (ideally zero (0.0)), to obtain Data which allows reliable calculation DELTA values. That is, Polarization State sensitivity to Sample System Optical and Physical properties drops quickly when the (AOI) is varied from seventy-five (75) degrees. The present invention, however, allows use of an (AOI) of thirty (30) degrees, (and other (AOI's)), with essentially no loss of said sensitivity. This is, as those experienced in the field of ellipsometry will immediately recognize, is surprising and significant, emphasis added.

2. Use of the Case 4 VASE-C Mode to measure DELTA Values where the (AOI) is near the angle at which DELTA quickly changes from near one-hundred-eighty (180) degrees to zero (0.0) degrees. The case investigated by the Inventors involved a thick BK7 Glass Sample System. The optical (AOI) is between fifty-six (56) and fifty-eight (58) degrees. The very surprising result is that PSI and DELTA Data in the obtained regions from fifty-five (55) to fifty-six (56) degrees and from fifty-seven (57) to fifty-eight (58) degrees is sufficiently accurate to allow calculation of Thin Film roughness, losses, thickness and Optical Refractive Index therefrom. Those knowledgeable in the field of Ellipsometry will recognize the surprising nature of this as previously DELTA's associated with the identified (AOI) ranges were not measurable with sufficient accuracy using Rotating Element Ellipsometers (REE's), (eg. (RAE), (RPE) etc.).

It is felt that Patentable material is presented herein in both System and Method Categories. The System which allows multidirectional "Tilt" of Berek-type Retarder(s), which Retarders are positioned as described infra in Ellipsometer Systems, is considered new, novel, nonobvious and useful in the context of Ellipsometer Systems. For instance, the Inventors are unaware of any mounting system for a Berek-Type Variable Retarder which allows more than one direction of "Tilt" for use in any context. It is also felt that the Method of use of any Retarder System(s), which are Continuously Variable over a relatively large spectroscopic range of wavelengths, positioned as described infra, in Ellipsometer Systems to allow setting ellipsometric BETA in a range in which it is relatively insensitive to noise and errors in measurement etc. thereof, so that Transfer Functions which allow determination of PSI and DELTA from a measured ellipsometric ALPHA and ellipsometric BETA are not unusably sensitive to noise and errors in the measurement etc. of ellipsometric BETA, also meets the criteria for Patentability, (particularly where the Case 4 VASE-C Mathematical Regression approach to PSI and DELTA is utilized).

It is further felt that the use of a "Mathematical Regression" as applied to a multiplicity of ellipsometric ALPHA-ellipsometric BETA pair values, to arrive at PSI and DELTA values, is new, novel, nonobvious and useful. This is felt to be the case whether ellipsometric BETA value range control is utilized or not in obtaining ellipsometric BETA values. That is, whether a Case 2 No-Plate Regression or Case 4 VASE-C Mode, respectively is practiced. Also, as described infra, said Case 2 and Case 4 Modes utilizes well known "Mathematical Regression" approaches to arrive at PSI and DELTA values, provided an array of measured ellipsometric ALPHA and ellipsometric BETA values. Such can be considered as an "indirect", as opposed to a "direct" means for determining PSI and DELTA. In a "direct" approach singular ellipsometric ALPHA and ellipsometric BETA values are simply plugged directly into Eqs. 2 and 3, for instance, and PSI and DELTA simply calculated. A number of so directly determined PSI and DELTA values can be averaged, and the approach is still considered a "direct" approach. A Regression approach, however, briefly, utilizes an array of ellipsometric ALPHA and ellipsometric BETA values, and finds PSI and DELTA values which correspond to a Least Mean or Least Square Error, for instance, "fit" to said ellipsometric ALPHA and ellipsometric BETA data.

It is also believed that the capability of the present invention system to include one or more Variable Retarder(s) in an Ellipsometer System, the presence of which can be made essentially "transparent" to an end use by the multi-direction "Tilt" capability which allows alignment of an Incident Beam of Light essentially "exactly" with the Optical Axis of a Berek-Type Variable Retarder, is in itself strong evidence of Patentability. To date only one direction of "Tilt" has been possible with commercially available Berek-Type Variable Retarder mounting means. While one direction of "Tilt" can allow adjustment of a Variable Retarder sufficient for most applications, the present invention extended the capability of Ellipsometers generally, to allow degrees of precision not heretofore available. The present multi-tilt capability allows adjusting out the effect of imperfections in Retarder(s) (eg. out of parallel surfaces and bulk defects etc.), which imperfections vary from Variable Retarder to Variable Retarder as received from a manufacturer. That is, an Ellipsometer can be custom adjusted to eliminate imperfections resulting from imperfections in a specific Retarder included therein, which imperfections vary from Variable Retarder to Variable Retarder.

Continuing, a Rotating Analyzer Ellipsometer (RAE) was used as an example in the foregoing, it is to be understood that the foregoing discussion is entirely applicable to Rotating Polarizer Ellipsometer (RPE) Systems where the functions of the Analyzer, (which becomes a non-rotating element (A)), and Polarizer, (which becomes a Rotating Polarizer (RP)), are simply reversed. That is, in a Rotating Polarizer Ellipsometer (RPE) there is present a Rotating Polarizer (RP) and an Analyzer (A), rotation of which Analyzer (A) sets its Azimuthal Angle which is the ellipsometric ALPHA determining parameter, (identified as (ANL)), equivalent to (POL) in the foregoing. In a Rotating Analyzer Ellipsometer then, a Polarizer sets a Polarization State and a Rotating Analyzer analyzes changes in such effected by interaction with a Sample System. In a Rotating Polarizer Ellipsometer, the Rotating Polarizer sets an continuous array of Polarization States and a Stationary Analyzer interprets changes in such effected by interaction with a Sample System.

As well, while the equations corresponding to Eqs. 1, 2, 3 and 4, herein, (which corresponding equations are not presented herein), are somewhat different in other than Rotating Analyzer and Rotating Polarizer Ellipsometers, the foregoing discussion is generally applicable to any Ellipsometer System which contains a Rotating Element, (such as a Rotating Compensator Ellipsometer, and a Rotating Analyzer and Polarizer and Fixed Compensator Ellipsometer).

Continuing, the present invention can also be beneficially applied to Rotatable Element Nulling Ellipsometer (RENE) Systems, including Automated versions (REANE). A typical Rotatable Element Nulling Ellipsometer (RENE) System can be visualized by reference to FIG. 2, with the Rotating Analyzer (RA) being interpreted as a "Rotatable" Analyzer. Use of a (RENE) System involves providing a Beam of Light from a Light Source (LS), causing it to become Linearly Polarized by passage through a Polarizer (P), (which is also "Rotatable"), and then through a Compensator, (positioned as is (VR1) in FIG. 2, but typically being a fixed wavelength Rotatable Azimuth Retarder), prior to interacting with a Sample System (SS). Light reflecting from said Sample System (SS) passes through said "Rotatable" Analyzer (RA) and enters a Detector (DET) System. In use the Azimuths of said "Rotatable" Polarizer (P), Fixed Wavelength Rotatable Azimuth Retarder, (positioned as is (VR1) in FIG. 2), and Rotatable Analyzer (RA) are set so that the Detector reads a Minimum Value. A number of said "Null" readings can be obtained at a number of Polarizer Settings, (typically at (±forty-five degrees with respect to one another), and a Transfer Function utilized to arrive as a Sample System PSI and DELTA. (This is well described in the Azzam and Bashara reference previously cited on pages 158–169, which reference is incorporated by reference hereinto). A purpose of the Compensator is to enter a Retardance to one quadrature component of a polarized beam of light passing therethrough with respect to the other thereof. However, prior to the present invention, accurate direct control of a Variable amount of quadrature component Retardance, over a relatively large spectroscopic range, was essentially impossible because of resolution problems, and because of the requirement that (RENE) Compensator elements be changed when a widely varying range of wavelength investigated was changed. Because of better adjustment resolution capability, elements which could be adjusted by changing Azimuth settings have been preferred. The present invention, particularly when embodied using one or more BEREK-type Variable Retarder(s), however, overcomes the Resolution difficulties associated with setting quadrature component phase angle differeneces. And, as described elsewhere in this Disclosure, the BEREK-type Variable Retarder can provide Variable Retardance over a wide range of wavelengths because its Optical axis, being essentially perpendicular to a surface thereof, is not manufactured for application over only a relatively small range of wavelengths. Simply tilting said BEREK-type Variable Retarder, (rather than replacing it), in one or more planes, effectively configures it for operation at a desired wavelength over a relatively large range thereof, and said "Tilting" also directly controls the amount of Retardance provided thereby to quadrature-orthogonal components of a polarized beam of light, at a desired wavelength. As stated in the Azzam and Bashara reference, in Footnote 9 on page 166 thereof, prior attempts at achieving the result enabled and provided by the present invention, (ie, accurate Direct Control of Compensator effected phase angles between orthogonal-quadrature components of polarized beams of light, over a relatively large range of wavelengths), have failed because the Retardation Resolution of previously utilized Variable Retarders was about two orders of magnitude poorer than the resolution associated with setting Polarizer, Analyzer and Compensator Azimuth angles.

Retardation Resolution provided by BEREK-type Variable Retarders (VR's), however, is comparable to that associated with the setting of said Azimuths, emphasis added. Also said BEREK-type Variable Retarders can be tilted in multiple directions, (ie. about multiple axes), and be made to appear end-user transparent in (RENE) Systems, just as in other, previously described, Ellipsometer Systems.

Figures 8, 9:
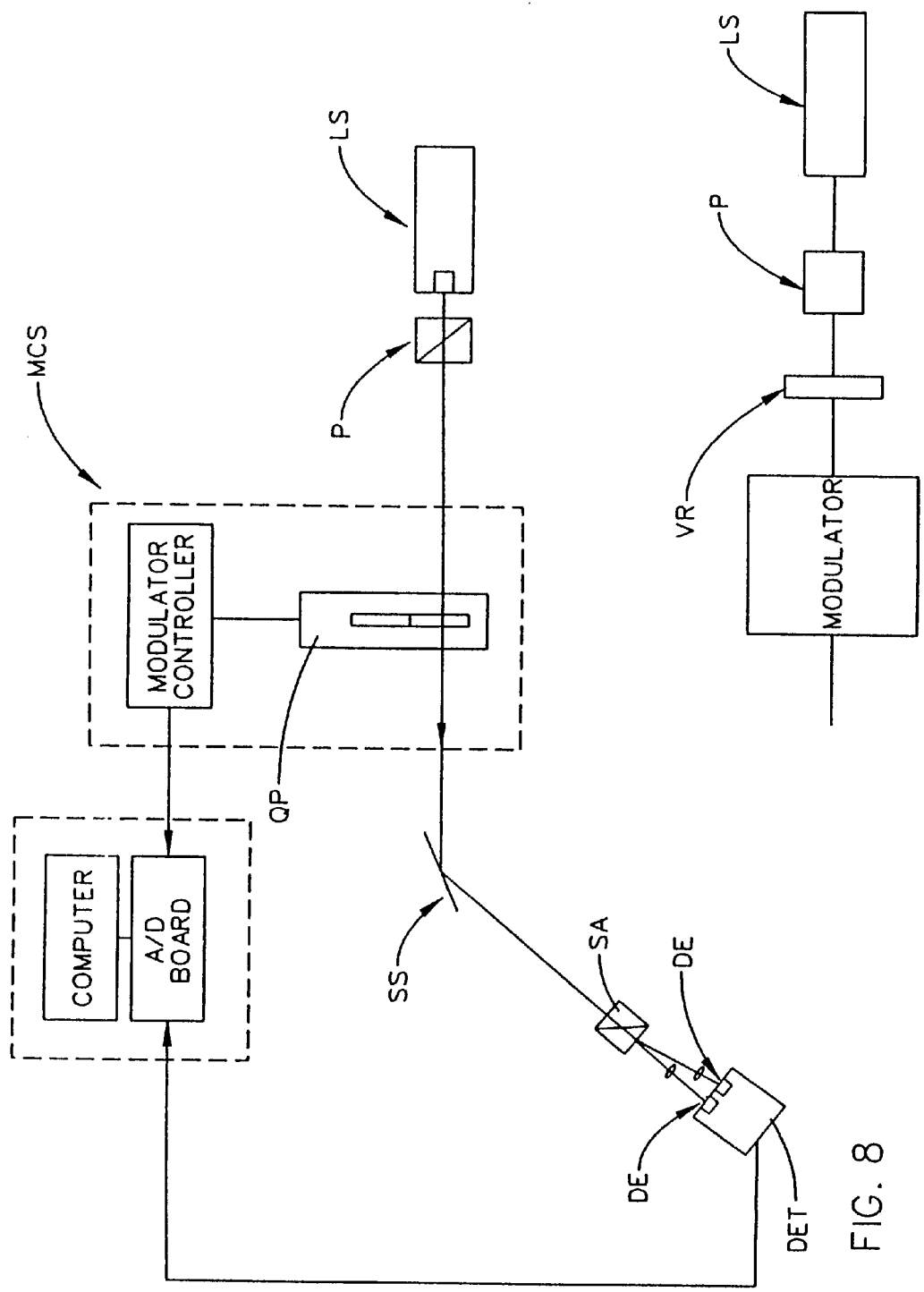
FIG. 8 shows a basic Modulation Ellipsometer System.
FIG. 9 shows a portion of the basic Modulation Ellipsometer System of FIG. 8 including a present invention Variable Retarder.

In addition, it must be specifically stated that the foregoing discussion regarding application of Variable Retarders (VR's) to Rotatable Element Nulling Ellipsometer (RENE) Systems and Rotating Element Ellipsometer (REE) Systems to optimize their operation, is also generally applicable to Modulation Element Ellipsometers MEE's). FIG. 8 shows an example of a typical Modulation Element Ellipsometer (MEE). Shown are a Light Source (LS), followed by a Polarizer (P). During use, a polarized beam of light emerging from said Polarizer (P) enters a Modulator Controller System (MCS) which, via a Quartz Rod (QR), for instance, serves to polarization state modulate said Polarized beam of light. Said modulated beam of Polarized light then encounters and interacts with a Sample System (SS), said interaction serving to affect the Polarization State of said modulated polarization state modulated beam of light. A Split Analyzer (SA) then serves to direct quadrature components of said polarization state modulated polarized beam of light into a Dual Analyzer (DA) system. Signals from said Dual Analyzer (DA) are then subjected to separate Fourier Analysis procedures by way of, for example, an A/D Board and Computer system. FIG. 9 shows a partial view of FIG. 8, demonstrating a Variable Retarder (VR) of the present invention entered thereto. It is noted that said Variable Retarder (VR) can be entered at functionally equivalent locations in the FIG. 8 representation of a Modulation Ellipsometer and FIG. 9 is not to be interpreted as limiting.

Continuing, Modulation Ellipsometers have difficulty measuring PSI and DELTA for Sample Systems which provide PSI values near forty-five (45) degrees, and which, (as in RAE's for instance), provide DELTA values near zero (0) or one-hundred-eighty (180) degrees, (and additionally where DELTA is near ninety (90) degrees). While the range in which PSI measurement difficulties are encountered are somewhat different, as compared to Rotating Element Ellipsometers, (see infra), the underlying problem is equivalent. That being that Ellipsometer Systems in general are insensitive to and unable to accurately measure Sample System PSI and DELTA values in certain ranges thereof.

As alluded to infra, it is to be understood that Modulation Ellipsometers operate by Modulating Quadrature Components of an electromagnetic beam utilized in the investigation of a Sample System, (which can be "P" and "S" Components), which electromagnetic beam is caused to interact with a Sample System during use. Utilization of one type of Modulation Ellipsometer requires that Quadrature Components be separately subjected to Fourier Analysis to provide Fourier Series Coefficients therefore, as shown by Equations 5.

$$VA = VA0 + VA1*COS(WT) + VA2*COS(2*WT) +$$
$$VA3*COS(3*WT) + VA4*COS(4*WT) + ...$$

EQNS. 5

$$VB = VB0 + VB1*COS(WT) + VB2*COS(2*WT) +$$
$$VB3*COS(3*WT) + VB4*COS(4*WT) + ...$$

Now, certain of the Fourier Series Coefficients from each Quadrature Component representing Fourier Series are, it is to be realized, found to become insensitively small, and even vanish, where a measure Sample System PSI is near forty-five (45) degrees and certain of said Fourier Series Coefficients are found to become insensitively small, and even vanish, where a measured Sample System DELTA is near zero ((0) or ninety (90), or one-hundred-eighty (180) degrees. Continuing, the Fourier Series Coefficients which become insensitively small, or even vanish, where PSI is near forty-five (45) degrees or where DELTA is near zero (0), ninety (90), or one-hundred-eighty (180) degrees are utilized in equations which determine a Sample System PSI and/or DELTA. The math involved, however, is very convoluted. That is, direct easily understood beam polarization state effect dependent describing Equations, such as Rotating Analyzer Ellipsometer, (RAE), representing Equations 3 and 4, see infra, are not readily available. However, Modulation Ellipsometer Systems, (eg. as demonstrated in FIG. 8), are amenable to a Jones Matrix analysis, from which relations between Fourier Coefficients of EQS. 6 can be uniquely related to a Sample PSI and DELTA. For instance, Equations 6 show functional dependence of various of the Equations 5, see infra, Modulation Ellipsometer Quadrature Component Fourier Series Coefficients for one type of Modulation Ellipsometer;

$$VA1 = 4*CA*(TAN(PSI))*(SIN(DELTA))*J1(M');$$
$$VA2 = 4*CA*(TAN(PSI))*(COS(DELTA))*J2(M');$$
$$VB1 = -4*CB*(TAN(PSI))*(SIN(DELTA))*J1(M');$$
$$VB2 = 4*CB*(-TAN(PSI))*(COS(DELTA))*J2(M');$$

EQNS. 6 where CA and CB are calculated from equations such as Equations 7, $$CA=((4*VA2+VA1*M+(VA0-VA2)*M^2)/(2*M^2))$$
$$CB=((4*VB2+VB2*M+(VB0-VB2)*M^2)/(2*M^2))$$

EQNS. 7 and where J1(M') and J2(M') are Bessel Functions of the First and Second kind, respectively, evaluated at (M'), where (M') is arrived at by solution of a trancendental equation such as Equations 8;

$$VA1*J3(M') = -VA3*J1(M');$$
$$VB1*J3(M') = -VB3*J1(M');$$

EQNS. 8 where J3(M') is a Bessel Function of the Third kind evaluated at M'.

Now, Equations for calculating PSI and DELTA values, which Equations utilize above Equations 5, 6, 7 and 8, or similar Equations, are represented by Equations 9;

$$SIN(DELTA) = \frac{2(((COS(DELTA) * VA1 * VB1 * J2(M'))}{((VA1 * VB2 + VA2 * VB1) * J1(M'))};$$ EQNS. 9

$$(TAN(PSI))^2 - U * (TAN(PSI)) + 1 = 0;$$

where $U = (2 * A * (B * C + 2 * D)) * J2(M'))/(VA1 * VB2 + VA2 * VB1);$ and where $A, B, C,$ AND $D$ are;

$$A = (COS(DELTA))$$
$$B = (J0(M') + 1)$$
$$C = (VA2 * VB1 - VA1 * VB2)$$
$$D = (VA0 * VB1 - VA1 * VB0) * J2(M')$$

Inspection of the above Equations 6 immediately reveals that at DELTA values of zero (0) or one-hundred-eighty (180) degrees, Fourier Series Quadrature Component Coefficients VA1 and VB1 become zero (0) because of their SIN(DELTA) functional dependence. Note also the VA2 and VB2 Fourier Series Quadrature Component Coefficient dependence on the COS(DELTA) function leads to VA2 and VB2 becoming zero (0) at DELTA equal to ninety (90) degrees. Continuing, inspection of Equations 9, show that said Quadrature Components Coefficients are VA1, VB1, VA2 and VB2 are required to allow evaluation of PSI and DELTA. Hence, where a Sample System presents with a DELTA value of near zero (0) or ninety (90) or one-hundred-eighty (180) degrees, it is to be expected that the Modulation Ellipsometer will encounter problems in providing accurate measurements. Equivalent, less obvious, analysis can be applied to show that where a Sample System presents with PSI values in the range of forty-five (45) degrees, a similar problem exists.

Suffice it to say that the present invention Variable Retarder (VR), can be considered as a means by which a Sample System per se. can be made to "appear" to a Modulation Ellipsometer System, as of it has a PSI and/or DELTA in a range in which such can be accurately measured by a Modulation Ellipsometer. That is, the present invention Variable Retarder (VR) can be thought of as serving to comprise a part of a "Composite Sample System", said Composite Sample System consisting of a Sample System per se. to be investigated, in series, (as encountered by the investigatory electromagnetic beam), with the Variable Retarder (VR). In use a PSI and DELTA of a resulting "Composite Sample System" can be measured, said measured PSI and DELTA values being in ranges which can be accurately measured by a Modulation Ellipsometer, with the effects of a known (VR) adjustment, (such as a known "Tilt" angle where a Berek Retarder is utilized), being compensated (eg. subtracted therefrom or otherwise), to provide PSI and DELTA values for an investigated Sample System per se. In the past researchers have provided a ninety (90) degree retarder to a Modulation Ellipsometer System, (see U.S. Pat. No. 5,416,588 to Ducharme et al. titled "SMALL MODULATION ELLIPSOMETER"), to shift a Composite Sample System PSI sensitivity to allow measurement of Sample System per se. which presents with a PSI of near ninety (90) degrees, and/or a DELTA of near zero (0) or one-hundred-eighty (180) degrees. However, the nature of the math applicable to describing Modulation Ellipsometer operation then leads other difficulties. What is required to allow optimizing the operation of Modulation Ellipsometers is the capability of introducing an easily adjusted Variable Retardance between the Polarizer and Analyzer thereof, just as is the case with (REE's). In addition, it is also noted that it is possible to provide simultaneous Variable Retardance, and adjustment of a Modulation Ellipsometer Polarizer, (and/or Analyzer), to effect optimum operation. As considered in the discussion with respect to (REE's), simultaneous adjustment of both Polarizer, (and/or Analyzer), and Variable Retarder (VR), allows setting an optimum state of electromagnetic beam polarization.

(Note, the above example provides for use of Fourier Series Coefficients obtained from two Polarized Light Beam Quadrature Components. Some Modulation Ellipsometers (ME's), however, utilize Fourier Series Coefficients from only one such Quadrature Component. The above example is, thus, not to be considered as limiting).

As just mentioned, in the discussion pertaining to (REE's) infra, the concept of controlling the "Polarization State" in an electromagnetic beam utilized in the investigation of a Sample System per se. was presented. It should be understood, however, that the concept of forming a "Composite Sample System" comprising a seriesed combination of a Sample System per se. and a Variable Retarder (VR), as presented regarding the explanation of the application of the present invention (VR) to Modulation Ellipsometers, can also be of use in comprehending the operation of (REE's) where a present invention (VR) is present. That is, regardless of Ellipsometer System type, one can conceive of the effect of applying a present invention (VR) as that of setting a "Polarization State" in an investigative Ellipsometer System electromagnetic beam, or as serving to provide a "Composite Sample System" which is comprised of the Sample System per se. and the (VR) in series, (as encountered by an investigative electromagnetic beam in an Ellipsometer System). Regardless of how viewed, the result of applying the present invention (VR) is that measured PSI and DELTA values of an effective Composite Sample System by an investigative electromagnetic beam in certain Polarization State, are caused to be within ranges wherein measurement thereof can be performed by the Ellipsometer System, regardless of type, with actual Sample System per se. PSI and DELTA values then being arrived at by compensating (eg. subtracting out or otherwise), the effect of a known (VR) setting, on the measured PSI and DELTA values. In use, optimum (VR) settings effecting an "Optimum Electromagnetic Beam Polarization State", (or as alternatively stated an "Optimum Composite Sample System"), can be established within an Ellipsometer System of any type, such that measured PSI and DELTA values are placed in ranges which can be accurately measured, with Sample System per se. values then being arrived at by mathematically compensating (eg. subtracting out or otherwise), the known effect of the (VR), and perhaps the rotation of a Polarizer of Analyzer.

It should then be appreciated that the present invention (VR) system, and method of its use, are generally applicable to essentially any type Ellipsometer and/or Polarimeter and the like System, and Claims thereto are to be interpreted in said light.

It must also be mentioned that in the foregoing, Fourier Analysis has been cited as a typical approach to evaluation of, for instance, ellipsometric ALPHA and ellipsometric BETA Values in EQ. 1. It is to be understood that ellipsometric ALPHA and ellipsometric BETA are representations of a modulated intensity superimposed upon a constant Intensity signal provided by an Ellipsometer Detector System (DET). It is possible to arrive at representations of said modulated Intensity by other than Fourier Analysis. For instance an approach which utilizes digitizing is known as "Hadamard" Analysis. As well, least or mean square error curve fitting approaches can be utilized. Methods known as "Simplex" and "Newton-Ralphson" are examples of such approaches. The ellipsometric ALPHA and ellipsometric BETA terms, and PSI and DELTA determining Coefficients in general, are to be interpreted sufficiently broadly to include parameters arrived at by any such analysis approach, which parameters represent modulation of an intensity signal, for the purposes of Claim interpretation. It is to understood that similar comments are applicable to methods by which mathematical values for applicable Coefficients are arrived at in the application of any type of Ellipsometer System. (Numerical approaches to Coefficient determination are described in numerous text books, such as "NUMERICAL RECIPES IN C", Cambridge University Press, 1988, said reference being incorporated by reference into this Disclosure).

It is pointed out that the terminology "zero, and multiple-order-waveplate" has been used throughout this Disclosure in referral primarily to other than Berek-type (VR's), (note that Berek-type Retarders also provide a zero-order operational range). Said usage was to draw attention to the fact that the Berek-type Variable Retarder can be easily utilized over greater than a zero-order angular range, (ie. zero (0) to three-hundred-sixty (360) degrees), in the present invention, and also, because the Retardance Curve vs. angle for many non-Berek type retarders, in the first and higher orders, is not simply a repeat of that at the zero order. Where a non-Berek Retarder does provide a non-abberated repeat curve of Retardance vs. angle in above zero-order angular regions, they can possibly be used in the present invention in the higher order angular regions. In said case(s) all order Retardances vs. angle are to be considered as functionally equivalent to the zero-order, and for the purposes of Claim interpretation, covered within the terminology "zero-order".

The terminology "means for setting an angle of incidence" and the like includes the case of a system in which an angle of incidence is set only once, such at manufacture or at initial set-up. It does not imply that said means must be adjustable by a user during use.

As well, the terminology Spectroscopic Ellipsometer" or reference to the capability of an Ellipsometer as a "Spectroscopic" system, or as having the capability to operate over a spectroscopic range etc. is not to be interpreted as exclusionary of an Ellipsometer or Polarimeter and the like system which is operated at an essentially single wavelength. The Claims are to be interpreted to, include any Ellipsometer or Polarimeter and the like system regardless of specific operation parameters actually utilized in a Sample System investigation procedure. The present invention allows convenient use of a spectroscopic range of wavelengths and/or use of a wide range of Angles of Incidence (AOI's) with a single wavelength, for instance.

It is also noted that the terminology "Beam of Light" or "Light Beam" has been used in this Disclosure. Such is to be understood to mean "electromagnetic radiation" of any relevant wavelength, or range of wavelengths. As well, "an essentially single wavelength Beam of Light" is to be considered to be a small range of wavelengths centered about some wavelength. Such is typically encountered where a Detector Element (DE) selectively monitors a relatively small portion of a spectrum of wavelengths.

In addition, it is to be understood that the terminology "PSI and DELTA" refer to Sample System characterizing parameters, for Sample Systems which are isotropic, anisptropic, or anisotropic and depolarizing, wherein a Jones Matrix, a Jones Matrix with Off-Diagonal Terms or a Mueller Matrix applies respectively. The Claims are to be interpreted to include use of, and application to, any Ellipsometer or Polarimeter and the like system to any Sample System which can be inestigated thereby.

The Terminology "Rotating" and Rotatable" refer to Ellipsometer Elements, (Analyzers, Polarizers and Compensators), which constantly rotate during use, and which can be rotated during use if desired, respectively.

It is also noted that in the Claims, Sample Systems (SS's) are provided in Ellipsometer Systems. It is pointed out that Sample Systems are not elements of Ellipsometer Systems, but are recited in the Claims as "provided with" because to describe the operation of an Ellipsometer System requires the presence of a Sample System. The Claims are to be interpreted such that the making, using or selling of a Claimed Ellipsometer System, (including Polarimeter and the like Systems), without a Sample System present, would constitute Actual Infringement.

It is also noted that the terms "quadrature" and "orthogonal" are essentially equivalent.

Also it is to be understood that the terminology "compensate" does not necessarily imply an absolute. That is, where a procedure "compensates", (eg. "subtracts out or otherwise" removes, the effect of the presence of a Variable Retarder), the effect of said Variable Retarder presence is to be understood as "essentially eliminated", which can include, but does not necessarily require absolute elimination.

As well, the terminology "operable" over a spectroscopic range, as applied to a Variable Retarder (VR), implies it can provide required controlled, usable amounts of retardation between quadrature components of a polarized beam of light, over a relatively large spectroscopic range of wavelengths. That is to say that significant "Artifact" content which can not be easily compensated, is not simultaneously introduced to said beam of light by said Variable Retarder in use. In this regard Berek-type Variable Retarders have been emphasised as preferred embodiment present invention realization Variable Retarder Component(s) as they add minimal such "Artifacts" to polarized light beams passing therethrough in use. The terminology "Variable Retarder", or "Variable Retarder(s)", as used in the Claims, should be understood to, ideally, mean Low Artifact content introducing Components, with the Berek-type Variable Retarder being a preferred example thereof. Variable Retarders of other types, with essentially similar operting characteristics, are however, to be considered operably equivalent, within the scope, and applicable for use in realizing the present invention.

The terminology "Polarization State Generator" is also utilized in the Claims. It is to be understood that a "Polarization State Generator" does not necessarily have to completely impose a full Polarization State upon a beam of light. That is, setting, for instance, only the magnitude ratio of quadrature, (orthogonal), components is sufficient. As well, it is to be understood that, as utilized in the Claims, Polarization State Generators and Polarizers are to be understood to as capable of imposing any state of polarization upon a beam of light, (eg. linear, elliptical, essentially circular, circular, or even a lack of polarization).

It is also noted that "Artifact Content" as added to a polarized beam of light by a Variable Retarder, is considered sufficiently "low" for use in the present invention, if a Sample System PSI and DELTA values can, in the presence thereof, be determined to within a range of a few hundredths (0.01) of a degree or so by an ellipsometer or polarimeter and the like system utilizing the present invention.

Finally, it is to be understood that Polarimeters and the like are, in important respects, to be considered as essentially Ellipsometers which provide means by which the "Handedness" of a Polarized beam of Light can be determined. For the purposes of Claim interpretation, it is to be understood that the term "Ellipsometer", as fitted with at least one Polarized Beam Quadrature Component Phase Angle Range Control System, (eg. Variable Retarder), of the present invention, is, where appropriate, to be considered to be sufficiently broad to include "Polarimeter and the like Systems", without the need to recite such within every Claim. It is noted that such an interpretation is actually very much within conventional usage of the terminology involved. Also, the Terminology "and the like" shall be interpreted to mean, at a minimum, "functionally similar".

Having hereby disclosed the subject matter of this invention, it should be obvious that many modifications, substitutions, and variations of the present invention are possible in view of the teachings. It is therefore to be understood that the invention may be practiced other than as specifically described, and should be limited in breadth and scope only by the Claims.

We claim:

1. A method of reducing the sensitivity of modulation element ellipsometer (MEE) PSI and DELTA transfer functions to measured ellipsometric parameter values which is applicable over spectroscopic range, which method enables acquiring data from a (MEE) system which is of an accuracy and precision which allows calculation of sample system PSI and DELTA, even where other than the Brewster angle of incidence (AOI) of a polarized beam of light to a sample system is utilized, and even in the presence of at least one sample system condition selected from the group consisting of:

PSI is near forty-five (45) degrees;
DELTA is near zero (0.0); and
DELTA is near one-hundred-eighty (180) degrees;

which method also enables determination of the "Handedness" of a beam of polarized light utilized in said (MEE), said method comprising the steps of:

1. providing a (MEE) system which in use comprises:
   a. a polarization state generator system comprising:
      1. a source of a beam of light;
      2. a means for setting a polarization state in said beam of light;
   b. a polarized beam modulation element;
   c. a sample system; and
   d. a polarization state detector system comprising:
      1. an analyzer; and
      2. a detector system;

said polarized beam modulation element being positioned at a location selected from the group consisting of:

before and after said sample system;

which (MEE) further comprises at least one Berek-type variable retarder placed between said polarization state generator system, and said polarization state detector system; such that during use a beam of light is caused to exit said source of a beam of light, and have an ellipsometric parameter determining state of polarization effected therein by said means for setting a polarization state; which polarized beam of light is caused to interact with said sample system, and with said polarized beam modulation element, and with said at least one Berek-type variable retarder placed between said polarization state generator system and said polarization state detector system; which polarization state generator system can be adjusted to set a value of a first ellipsometric parameter and said at least one Berek-type variable retarder can be tilted, so as to set a value of a second ellipsometric parameter, such that said first and second ellipsometric parameters are in ranges in which a transfer function which mediates determining DELTA from said measured ellipsometric first and second parameters is relatively immune to noise and errors in said ellipsometric first and second parameters;

2. causing a beam of light to exit said source of a beam of light, and causing an ellipsometric first parameter setting state of polarization therein with said means for setting a polarization state;

3. causing said resulting polarized beam of light to interact with said sample system, and with said polarized beam modulation element, and with said at least one Berek-type variable retarder placed between said polarization state generator system and said polarization state detector system;

4. with said means for setting a state of polarization being adjusted to at least one setting and said at least one Berek-type variable retarder being adjusted to, sequentially, a plurality of tilt settings, obtaining ellipsometic first and ellipsometric second parameter values data;

and determining PSI and DELTA values utilizing said obtained ellipsometric first and ellipsometric second parameter values data by a mathematical technique that compensates adjustments made to said means for setting a state of polarization and said at least one Berek-type variable retarder on measured ellipsometric first and ellipsometric second parameter values.

2. A method of reducing the sensitivity of modulation element ellipsometer (MEE) PSI and DELTA transfer functions to measured ellipsometric parameter values which is applicable over spectroscopic range, which method enables acquiring data from a (MEE) system which is of an accuracy and precision which allows calculation of sample system PSI and DELTA, even where other than the Brewster angle of incidence (AOI) of a polarized beam of light to a sample system is utilized, and even in the presence of at least one sample system condition selected from the group consisting of:

PSI is near forty-five (45) degrees;

DELTA is near zero (0.0); and

DELTA is near one-hundred-eighty (180) degrees;

which method also enables determination of the "Handedness" of a beam of polarized light utilized in said (MEE), said method comprising the steps of:

1. providing a (MEE) system which in use comprises
   a. a polarization state generator system comprising:
      1. a source of a beam of light;
      2. a means for setting a polarization state in said beam of light;
   b. a polarized beam modulation element;
   c. a sample system; and
   d. a polarization state detector system comprising:
      1. an analyzer; and
      2. a detector system;
   said polarized beam modulation element being positioned at a location selected from the group consisting of:
      before and after said sample system;
   which (MEE) further comprises at least one variable retarder selected from the group consisting of:
      a. a system of at least two fixed-order-waveplate-type retarders which can be rotated with respect to one another, each about an axis perpendicular to an optical axes thereof, said optical axes being parallel to the surface of said fixed-order-waveplate-type retarders;
      b. a Babinet dual wedge-type variable retarder;
      c. a Soleil dual wedge-type variable retarder;
      d. a Kerr electro-optical-type variable retarder;
      e. a Pockels electro-optical-type variable retarder;
      f. a liquid crystal electro-optical-type variable retarder;
      g. a Voigt magnetic-faraday-effect variable retarder; and
      h. a Cotton-Mouton magnetic-faraday-effect variable retarder;
      i. a Berek-type variable retarder;
   said at least one variable retarder being placed between said Polarization State Generator system, and said Polarization State detector system, through which variable retarder said polarized beam of light must pass during use;

2. causing a beam of light to exit said source of a beam of light, and causing an ellipsometric first parameter setting state of polarization therein with said means for setting a polarization state;

3. causing said resulting polarized beam of light to interact with said sample system, and with said polarized beam modulation element, and with said at least one variable retarder placed between said polarization state generator system and said polarization state detector system, adjustment of said variable retarder serving to set a value of a second ellipsometric parameter;

4. with said means for setting a state of polarization being adjusted to at least one setting and said at least one Berek-type variable retarder being adjusted to, sequentially, a plurality of tilt settings, obtaining ellipsometric first and ellipsometric second parameter values data;

and determining PSI and DELTA values utilizing said obtained ellipsometric first and ellipsometric second parameter values data by a mathematical technique that compensates adjustments made to said means for setting a state of polarization and said at least one variable retarder on measured ellipsometric first and ellipsometric second parameter values.

3. A modulation element ellipsometer system (MEE) comprising:
   a. a polarization state generator system comprising:
      1. a source of a beam of light;
      2. a means for setting a polarization state in said beam of light;
   b. a polarized beam modulation element;
   c. a sample system; and
   d. a polarization state detector system comprising;
      1. an analyzer; and
      2. a detector system;
   said polarized beam modulation element being positioned at a location selected from the group consisting of:
      before and after said sample system;
   which (MEE) further comprises at least one Berek-type variable retarder placed between said polarization state generator system, and said polarization state detector system; such that during use a beam of light is caused to exit said source of a beam of light, and have an ellipsometric first parameter determining state of polarization effected therein by said means for setting a polarization state; which polarized beam of light is caused to interact with said sample system, and with said polarized beam modulation element, and with said at least one Berek-type variable retarder placed between said polarization state generator system and said polarization state detector system; which at least one Berek-type variable retarder can be tilted so as to set a value of an ellipsometric second parameter in a range in which a transfer function which mediates determining DELTA from a measured ellipsometric first parameter and ellipsometric second parameter values is relatively immune to noise and errors in said ellipsometric second parameter;
   said (MEE) being further comprised of computational means which performs said determination of said sample system PSI and DELTA, said determination of said sample system PSI and DELTA requiring input of data acquired with said ellipsometric second ellipsometric parameter value setting Berek-type variable retarder set in a plurality of tilt positions, which computational means compensates acquired data input thereto, for the effects of said required plurality of ellipsometric second parameter setting Berek-type variable retarder tilts.

4. A modulation element ellipsometer (MEE) system as in claim 3 in which the Berek-type variable retarder is mounted so as to simultaneously allow user directed tilt in more than one direction, said multiple tilt capability allowing a user to adjust said Berek-type retarder so that it has no effect, other than a negligible attenuation, on a beam of polarized light passing therethrough.

5. A ellipsometer element (MEE) system as in claim 3 which further comprises at least one additional element selected from the group consisting of:
   a. a stationary polarizer;
   b. a stationary analyzer;
   c. a stationary compensator;
   d. a rotating polarizer; and
   e. a rotating analyzer.

6. A modulation element ellipsometer system (MEE) comprising:

a. a polarization state generator system comprising:
1. a source of a beam of light;
2. a means for setting a polarization state in said beam of light;
b. a polarized beam modulation element;
c. a sample system; and
d. a polarization state detector system comprising;
1. an analyzer; and
2. a detector system;

said polarized beam modulation element being positioned at a location selected from the group consisting of:
before and after said sample system;
which (MEE) further comprises at least one variable retarder selected from the group consisting of:
a. a system of at least two fixed-order-waveplate-type retarders which can be rotated with respect to one another, each about an axis perpendicular to an optical axes thereof, said optical axes being parallel to the surface of said fixed-order-waveplate-type retarders;
b. a Babinet dual wedge-type variable retarder;
c. a Soleil dual wedge-type variable retarder;
d. a Kerr electro-optical-type variable retarder;
e. a Pockels electro-optical-type variable retarder;
f. a liquid crystal electro-optical-type variable retarder;
g. a Voigt magnetic-faraday-effect variable retarder;
h. a Cotton-Mouton magnetic-faraday-effect variable retarder; and
i. a Berek-type variable retarder;

such that in use said at least one variable retarder is placed between said polarization state generator system, and said polarization state detector system; such that during use a beam of light is caused to exit said source of a beam of light, and have an ellipsometric first parameter determining state of polarization effected therein by said means for setting a polarization state; which polarized beam of light is caused to interact with said sample system, and with said polarized beam modulation element, and with said at least one variable retarder placed between said polarization state generator system and said polarization state detector system; which at least one variable retarder can be adjusted so as to set a value of an ellipsometric second parameter in a range in which a transfer function which mediates determining DELTA from a measured ellipsometric first parameter and ellipsometric second parameter values is relatively immune to noise and errors in said ellipsometric second parameter;

said (MEE) being further comprised of computational means which performs said determination of said sample system PSI and DELTA, said determination of said sample system PSI and DELTA requiring input of data acquired with said ellipsometric second setting variable retarder set in a plurality of positions, which computational means compensates acquired data input thereto, for the effects of said required plurality of ellipsometric second parameter value setting variable retarder positions.

7. A modulation element ellipsometer (MEE) system as in claim 6 which further comprises at least one additional element selected from the group consisting of:
a. a stationary polarizer;
b. a stationary analyzer;
c. a stationary compensator;
d. a rotating polarizer; and
e. a rotating analyzer.

8. A method of determining sample system PSI and DELTA values by use of a modulation element ellipsometer (MEE) system, comprising the step of:

providing an (MEE) system which comprises
a. a polarization state generator system comprising:
1. a source of a beam of light;
2. a means for setting a polarization state in said beam of light;
b. a polarized beam modulation element;
c. a sample system effectively comprised of a sample system per se. and a variable retarder; and
d. a polarization state detector system comprising;
1. an analyzer; and
2. a detector system;

said polarized beam modulation element being positioned at a location selected from the group consisting of:
before and after said sample system;
which method further comprises the steps of
a. measuring a plurality of sample system ellipsometric first and ellipsometric second parameter pairs, as a function of at least one means for setting a polarization state in said beam of light setting(s), and a plurality of variable retarder settings; and
b. applying a mathematical technique to said plurality of measured ellipsometric first and ellipsometric second parameter pairs to determine PSI and DELTA values for said sample system per se. while compensating for the presence of said variable retarder.

9. A method of determining sample system PSI and DELTA values by use of a modulation element ellipsometer (MEE) system, comprising the step of:

providing an (MEE) system comprising:
a. a polarization state generator system comprising
1. a source of a beam of light;
2. a means for setting a polarization state in said beam of light;
b. a polarized beam modulation element;
c. a sample system; and
d. a polarization state detector system comprising;
1. an analyzer; and
2. a detector system;

said polarized beam modulation element being positioned at a location selected from the group consisting of:
before and after said sample system;
which (MEE) system further comprises a Berek-type variable retarder placed between said polarization state generator system, and said polarization state detector system; such that during use said Berek-type variable retarder can be tilted so as to set a value of an ellipsometric second parameter in a range in which a transfer function which mediates determining DELTA from a measured ellipsometric first parameter and ellipsometric second parameter is relatively immune to noise and errors in said ellipsometric second parameter, which method further comprises the steps of:
a. measuring a plurality of sample system ellipsometric first and ellipsometric second parameter pairs corresponding to, at each of at least one means for setting a polarization state in said beam of light setting(s), at least five Berek-type retarder settings, said Berek-type retarder settings including no-tilt, clockwise and counterclockwise elevational, and clockwise and counterclockwise azimuthal tilts; and
b. applying a mathematical technique to said plurality of measured ellipsometric first and second ellipsometric parameter pairs to determine sample system PSI and DELTA values, while compensating for presence of said at at least one Berek-type variable retarder.

10. A method of determining sample system PSI and DELTA values by use of a modulation element ellipsometer (MEE) system, comprising the step of:

providing an (MEE) system comprising:
  a. a polarization state generator system comprising:
    1. a source of a beam of light;
    2. a means for setting a polarization state in said beam of light;
  b. a polarized beam modulation element;
  c. a sample system; and
  d. a polarization state detector system comprising;
    1. an analyzer; and
    2. a detector system;
said polarized beam modulation element being positioned at a location selected from the group consisting of:
  before and after said sample system;
which (MEE) system further comprises at least one variable retarder selected from the group consisting of:
  a. a system of at least two fixed-order-waveplate-type retarders which can be rotated with respect to one another, each about an axis perpendicular to an optical axes thereof, said optical axes being parallel to the surface of said fixed-order-waveplate-type retarders;
  b. a Babinet dual wedge-type variable retarder;
  c. a Soleil dual wedge-type variable retarder;
  d. a Kerr electro-optical-type variable retarder;
  e. a Pockels electro-optical-type variable retarder;
  f. a liquid crystal electro-optical-type variable retarder;
  g. a Voigt magnetic-faraday-effect variable retarder; and
  h. a Cotton-Mouton magnetic-faraday-effect variable retarder;
  i. a Berek-type variable retarder;
said at least one variable retarder being placed between said polarization state generator system, and said polarization state detector system; such that during use said at least one variable retarder can be adjusted so as to set a value of ellipsometric second parameter in a range in which a transfer function which mediates determining DELTA from a measured ellipsometric first parameter and ellipsometric second parameter is relatively immune to noise and errors in said ellipsometric second parameter;
which method further comprises the steps of:
  a. measuring a plurality of sample system ellipsometric first and ellipsometric second parameter pairs as a function of at least one means for setting a polarization state in said beam of light setting(s), and a plurality of variable retarder settings; and
  b. applying a mathematical technique to said plurality of measured ellipsometric first and ellipsometric second parameter pairs to determine sample system PSI and DELTA values, while compensating for the presence of said at least one variable retarder.

11. An ellipsometer system selected from a group consisting of:
  modulation element, rotatable element and rotating element;
which ellipsometer system enables accurate and precise determination of PSI and DELTA values of essentially any investigatable sample system; said ellipsometer system comprising means for setting at least one polarization state in a beam of polarized light and means for identifying, and means for monitoring, a polarization state in said polarized beam of light, after an interaction thereof with a sample system;
  between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometic data;
  said ellipsometer system being further comprised of a computing system which performs determination of investigated sample system PSI and DELTA values, which computing system utilizes data obtained with said at least one adjustable means for controlling ellipsometric phase angle between orthogonal components in a polarized beam of light, being set to at least two selected settings, and which computing system performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values.

12. An ellipsometer system as in claim 11, in which at least one selection from the group consisting of:
  said means for setting at least one polarization state; and
  said means for identifying a polarization state in said polarized beam of light;
is an adjustable means for controlling an ellipsometric relative magnitude ratio of said orthogonal components, such that a plurality of ellipsometric relative magnitude ratios of said orthogonal components can be set thereby; and in which said computing system further performs compensation of any effects on obtained data resulting from adjustment(s) entered to ellipsometric relative magnitude ratios of said orthogonal components by said adjustable means for controlling an ellipsometric relative magnitude ratio of said orthogonal components in a polarized beam of light which is caused to interact with a sample system.

13. An ellipsometer system as in claim 12, in which said adjustable means for controlling an ellipsometric relative magnitude ratio of orthogonal component in a polarized beam of light comprises an adjustable polarizer.

14. An ellipsometer system as in claim 12, in which said adjustable means for controlling an ellipsometric relative magnitude ratio of orthogonal components in a polarized beam of light comprises an adjustable analyzer.

15. An ellipsometer system as in claim 11, in which said at least one adjustable means for controlling an ellipsometric phase angle between said orthogonal components in a polarized beam of light comprises a variable retarder.

16. An ellipsometer system as in claim 15, in which said variable retarder is Berek-type with its optical axis directed essentially perpendicular to a surface thereof, said Berek-type variable retarder being mounted in said ellipsometer system so as to allow it to be tilted about multiple axes thereby enabling it to provide variable amounts of retardance between orthogonal components in a beam of polarized light caused to pass therethrough, and so that optical axis can be caused to be aligned with said polarized beam of light with the result being that said Berek-type variable retarder becomes essentially end-user "transparent", without removal of said Berek-type variable retarder from said ellipsometer system.

17. An ellipsometer system as in claim 15, in which said variable retarder is selected from the group consisting of:
   a. a system of at least two fixed-order-waveplate-type retarders which can be rotated with respect to one another, each about an axis perpendicular to an optical axes thereof, said optical axes being parallel to the surface of said fixed-order-waveplate-type retarders;
   b. a Babinet dual wedge-type variable retarder;
   c. a Soliel dual wedge-type variable retarder;
   d. a Kerr electro-optical-type variable retarder;
   e. a Pockels electro-optical-type variable retarder;
   f. a liquid crystal electro-optical-type variable retarder;
   g. a Voigt magnetic-faraday-effect variable retarder; and
   h. a Cotton-Mouton magnetic-faraday-effect variable retarder.

18. An Ellipsometer system as in claim 11, in which said at least one adjustable means for controlling an ellipsometric phase angle between said orthogonal components in a polarized beam of light has the capability of providing functional retardation between orthogonal components in a polarized beam of light over a spectroscopic range of at least two-hundred-thirty (230) to seventeen-hundred (1700) nanometers.

19. A method of determination of sample system PSI and DELTA values with improved accuracy and precision comprising, in a functional order, the steps of:
   a. providing an ellipsometer system selected from the group consisting of:
      modulation element, rotatable element and rotating element;
   which ellipsometer system enables accurate and precise determination of PSI and DELTA values of essentially any investigatable sample system; said ellipsometer system comprising means for setting at least one polarization state in a beam of polarized light and means for identifying, and means for monitoring, a polarization state in said polarized beam of light, after an interaction thereof with a sample system;
   between said means for setting at least one polarization state in a beam of polarized light and said means for monitoring a polarization state in said polarized beam of light, there being present at least one adjustable means for controlling an ellipsometric phase angle between orthogonal components in a polarized beam of light, which adjustable means for controlling an ellipsometric phase angle, in use, allows sequentially setting a plurality of ellipsometric phase angles between orthogonal components in a polarized beam of light which is caused by said ellipsometer system to interact with a sample system, such that in use said ellipsometric phase angle can be set sequentially through a plurality of settings while ellipsometric data is obtained by said means for monitoring a polarization state in said polarized beam of light at at least two selected settings of said at least one adjustable means for controlling an ellipsometric phase angle; which obtained ellipsometric data can be utilized in determination of PSI and DELTA values of an investigated sample system, where said determination of said PSI and DELTA values includes compensating for the effects on said obtained ellipsometric data of said at least two selected setting of said at least one adjustable means for controlling an ellipsometric phase angle, on said obtained ellipsometic data;
   said ellipsometer system being further comprised of a computing system which performs determination of investigated sample system PSI and DELTA values, which computing system utilizes data obtained with said at least one adjustable means for controlling ellipsometric phase angle between orthogonal components in a polarized beam of light, being set to at least two selected settings, and which computing system performs compensation of the effects of said at least one adjustable means for controlling ellipsometric phase angle between orthogonal components, on said utilized ellipsometric data obtained at said at least two selected settings of said at least one adjustable means for controlling ellipsometric phase angle between orthogonal components, in determining sample system PSI and DELTA values;
   b. placing a sample system to be investigated into said ellipsometer system and causing a beam of polarized light from said means for setting at least one polarization state in a beam of polarized light to interact therewith and enter said means for monitoring a polarization state;
   c. adjusting said at least one adjustable means for controlling ellipsometric phase angle between said orthogonal components to be sequentially set to a plurality of settings while ellipsometric data is obtained by said means for monitoring a polarization state in said polarized beam of light at at least two selected settings from said plurality settings of said at least one adjustable means for controlling a value of ellipsometric phase angle between said orthogonal components;
   d. causing said computing system to determine investigated sample system PSI and DELTA values by a method which performs compensation of the effects of said at least one adjustable means for controlling ellipsometric phase angle between orthogonal components in a polarized beam of light on said ellipsometric data obtained at said at least two selected settings of said at least one adjustable means for controlling ellipsometric phase angle between orthogonal components in a polarized beam of light which is caused to interact with a sample system, in determining sample system PSI and DELTA values; and
   e. optionally determining at least some of members of the group consisting of:
      the "Handedness", Stokes Vector, and Jones and Mueller Matrix components;
   of said polarized beam of light and investigated sample system.

20. A Method of determination of sample system PSI and DELTA values as in claim 19, in which data comprising a plurality of relative magnitude ratios of orthogonal components and phase angles between orthogonal components are obtained, at least some of which plurality of ellipsometric relative magnitude ratios of orthogonal components and measured ellipsometric phase angles between orthogonal components correspond to sequential adjusted settings of ellipsometric relative magnitude ratios of orthogonal components present in said beam of polarized light, said sequential adjusted settings being effected by adjustment of at least one member of the group consisting of:

said means for setting at least one polarization state in a beam of polarized lights; and said means for identifying a polarization state in said polarized beam of light;

and in which said computing system is also caused to perform compensation of the effects of said sequential adjusted settings of ellipsometric relative magnitude ratios of orthogonal components present in said beam of polarized light which is caused by said ellipsometer system to interact with a sample system, in determining investigated sample system PSI and DELTA values.

21. A method of determination of sample system PSI and DELTA values as in claim 20, in which a plurality of ellipsometric phase angles between orthogonal components are effected at each sequential adjusted setting of ellipsometric relative magnitude ratio of orthogonal components present in said beam of polarized light which is caused by said ellipsometer system to interact with a sample system.

* * * * *